(12) United States Patent
Miyamoto et al.

(10) Patent No.: US 8,853,630 B2
(45) Date of Patent: Oct. 7, 2014

(54) SCANNING ELECTRON MICROSCOPE AND A METHOD FOR IMAGING A SPECIMEN USING THE SAME

(71) Applicant: Hitachi High-Technologies Corporation, Tokyo (JP)

(72) Inventors: Atsushi Miyamoto, Yokohama (JP); Wataru Nagatomo, Yokohama (JP); Ryoichi Matsuoka, Yotsukaido (JP); Hidetoshi Morokuma, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/166,884

(22) Filed: Jan. 29, 2014

(65) Prior Publication Data

US 2014/0145078 A1    May 29, 2014

Related U.S. Application Data

(63) Continuation of application No. 13/432,176, filed on Mar. 28, 2012, now Pat. No. 8,642,957, which is a continuation of application No. 11/673,219, filed on Feb. 9, 2007, now Pat. No. 8,158,938.

(30) Foreign Application Priority Data

Feb. 17, 2006 (JP) ................................. 2006-040125

(51) Int. Cl.
*H01J 37/00*  (2006.01)
*H01J 37/26*  (2006.01)
*H01J 37/28*  (2006.01)
*G01N 23/20*  (2006.01)
*H01J 37/21*  (2006.01)

(52) U.S. Cl.
CPC ........... *G01N 23/20* (2013.01); *H01J 2237/216* (2013.01); *H01J 2237/2817* (2013.01); *H01J 2237/1532* (2013.01); *H01J 2237/1536* (2013.01); *H01J 37/265* (2013.01); *H01J 37/28* (2013.01); *H01J 37/21* (2013.01)
USPC ............ 250/307; 250/306; 250/310; 250/311

(58) Field of Classification Search
CPC ................... G06F 7/7065; G05B 2219/37441; H01J 2237/2817
USPC .................................. 250/306, 307, 310, 311
See application file for complete search history.

(56) References Cited

U.S. PATENT DOCUMENTS

| 7,801,353 B2 * | 9/2010 | Almogy et al. ................ 382/141 |
| 2004/0030430 A1 * | 2/2004 | Matsuoka ...................... 700/108 |
| 2006/0016992 A1 * | 1/2006 | Sato et al. ...................... 250/311 |

FOREIGN PATENT DOCUMENTS

| JP | 62-026835 | 2/1987 |
| JP | 2000-348658 | 12/2000 |

(Continued)

OTHER PUBLICATIONS

Japanese Office Action dated Mar. 13, 2012; Application No. JP2007-029928.

(Continued)

*Primary Examiner* — Michael Maskell
(74) *Attorney, Agent, or Firm* — Antonelli, Terry, Stout & Kraus, LLP.

(57) ABSTRACT

(1) part or all of the number, coordinates and size/shape and imaging sequence of imaging points each for observation, the imaging position change method and imaging conditions can be calculated automatically from CAD data, (2) a combination of input information and output information for imaging recipe creation can be set arbitrarily, and (3) decision is made of imaging or processing at an arbitrary imaging point as to whether to be successful/unsuccessful and in case a failure is determined, a relief process can be conducted in which the imaging point or imaging sequence is changed.

10 Claims, 15 Drawing Sheets

(56) References Cited

FOREIGN PATENT DOCUMENTS

| | | |
|---|---|---|
| JP | 2001-004328 | 1/2001 |
| JP | 2001-35893 | 2/2001 |
| JP | 2001-159616 | 6/2001 |
| JP | 2002-328015 | 11/2002 |
| JP | 2003-197138 | 7/2003 |
| JP | 2004-31709 | 1/2004 |
| JP | 2005-327578 | 11/2005 |
| WO | WO 01/63660 A1 | 8/2001 |

OTHER PUBLICATIONS

Japanese Office Action dated Jul. 24, 2012; Application No. JP2007-029928.

Japanese Office Action dated Aug. 20, 2013; Application No. JP2012-270904.

Japanese Office Action dated Aug. 27, 2013; Application No. JP2012-109073.

* cited by examiner

FIG. 2A
FIG. 2B
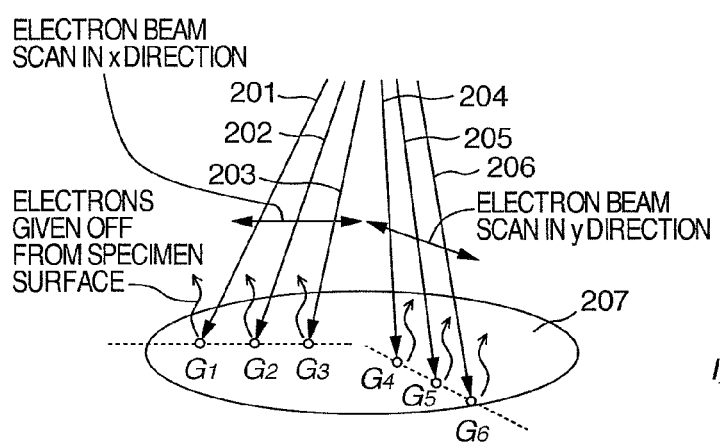
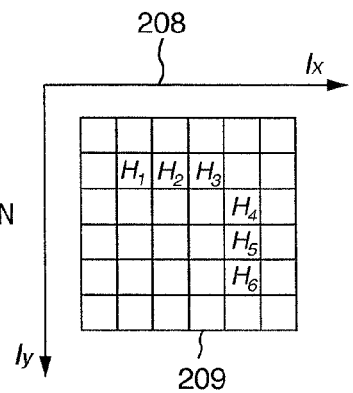

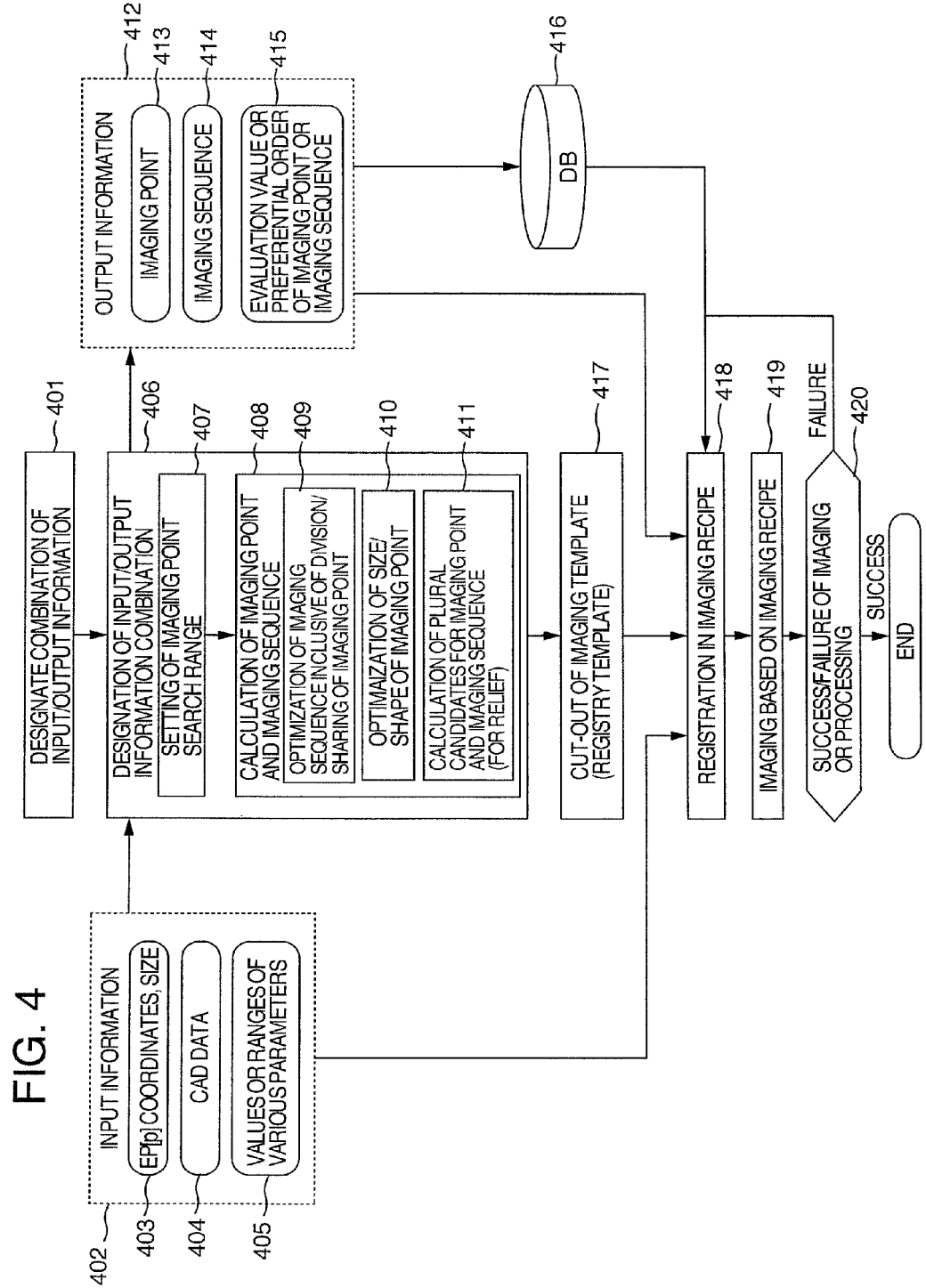

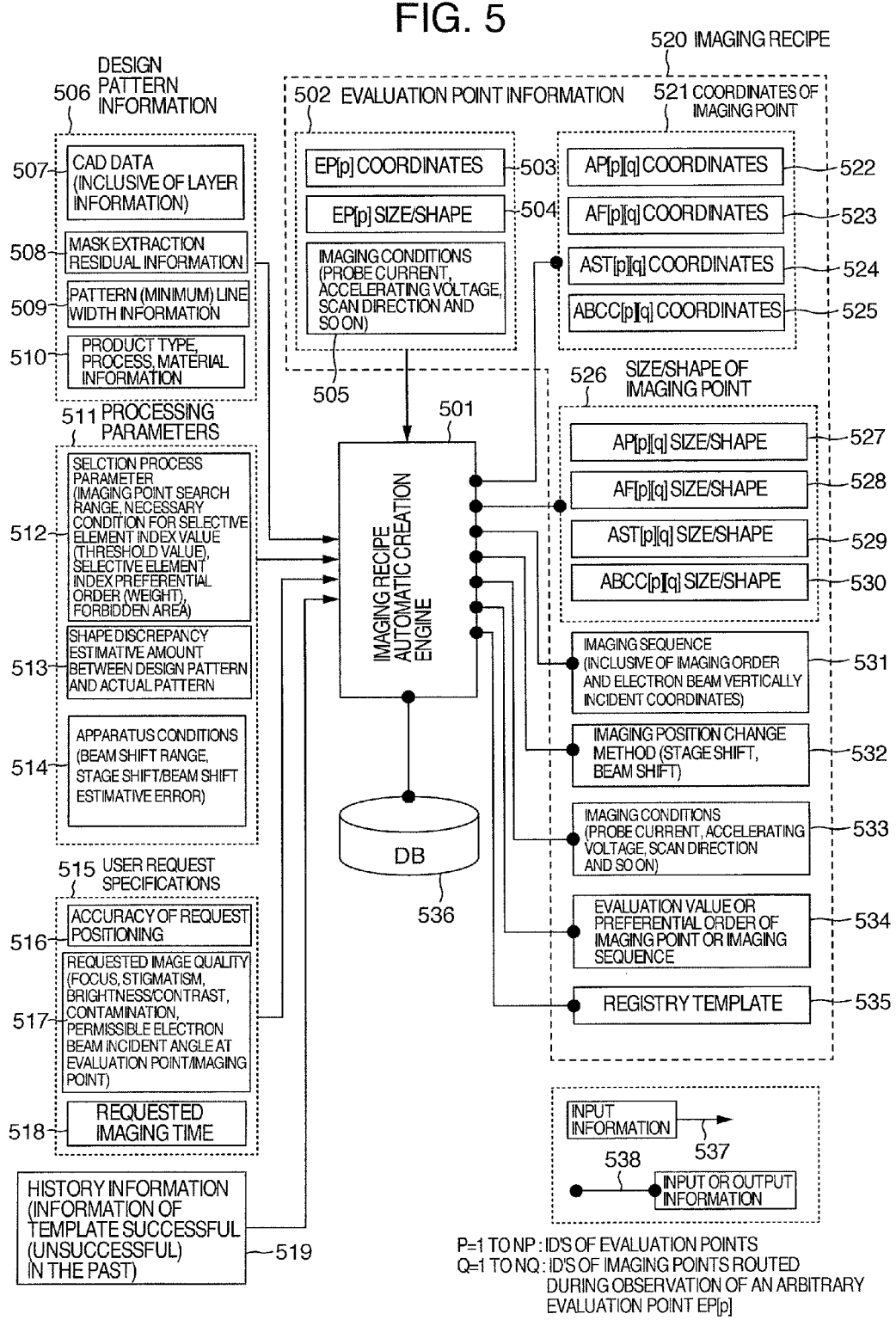

(a)   (b)

FIG. 12A
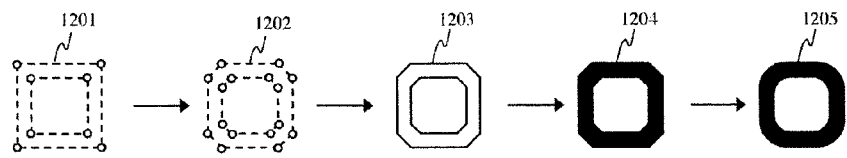
FIG. 12B
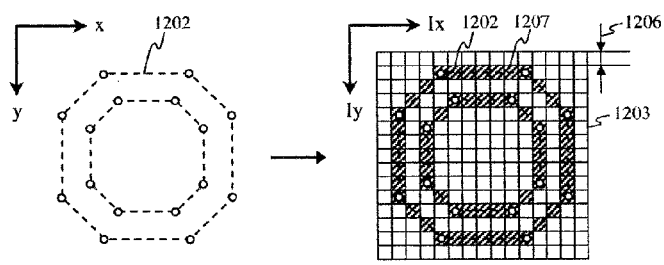
FIG. 13A
FIG. 13B
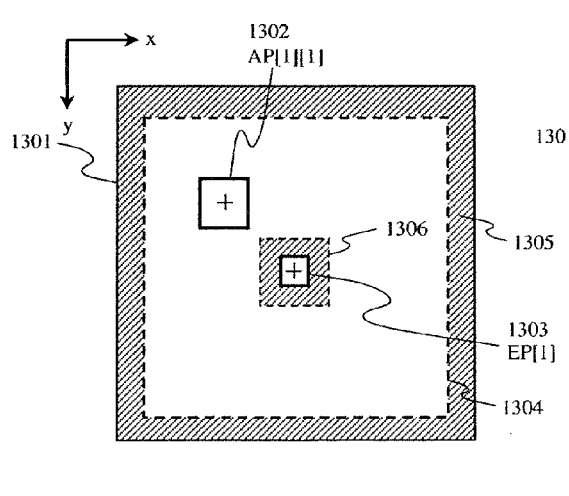
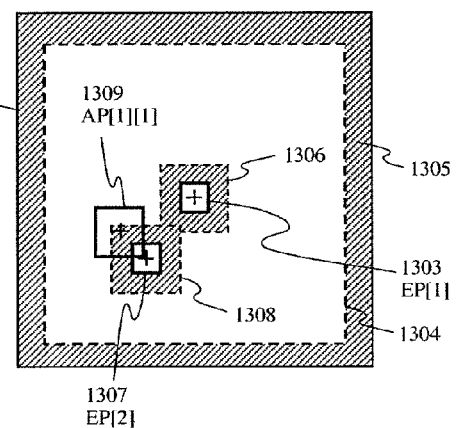

SCANNING ELECTRON MICROSCOPE AND A METHOD FOR IMAGING A SPECIMEN USING THE SAME

INCORPORATION BY REFERENCE

The present application is a continuation application of Ser. No. 13/432,176, filed Mar. 28, 2012, which is a continuation of Ser. No. 11/673,219 filed on Feb. 9, 2007, now U.S. Pat. No. 8,158,938, issued Apr. 17, 2012 which claims priority from Japanese application JP2006-040125 filed on Feb. 17, 2006, the content of which is hereby incorporated by reference into this application.

BACKGROUND OF THE INVENTION

The present invention relates to a scanning electron microscope (SEM) capable of automatically imaging an arbitrary evaluation point on a specimen and a method therefore and more particularly, to an SEM apparatus having the function to create and determine an imaging recipe automatically from circuit design data without using an actual wafer and a method therefore, the imaging recipe being necessary for observing an arbitrary evaluation point with high image quality and high accuracy. Registered in the imaging recipe are imaging parameters such as coordinates of an imaging point, size/shape (of an imaging area associated the imaging point but will be simply referred to as imaging point size/shape in the following description), imaging sequence of imaging points each for addressing, auto-focus, auto-stigmatism or auto-brightness contrast, imaging position changing method and imaging conditions and templates of evaluation points or imaging points as well.

For formation of a wiring pattern on a semiconductor wafer, a method is adopted, according to which a coating material called resist is coated on the semiconductor wafer, a mask for light exposure of the wiring pattern (reticle) is superimposed on the resist and rays of visible light or ultraviolet light or an electron beam is irradiated from above the reticle to expose the resist to light, thus forming the wiring pattern. The thus obtained wiring pattern changes in its pattern shape with either the intensity the irradiated visible ray, ultraviolet ray or electron beam has or the aperture and therefore, for formation of a highly accurate wiring pattern, maturity of the result of pattern needs to be inspected. For the inspection, a critical dimension scanning electron microscope (CD-SEM) has hitherto been used widely. A dangerous or critically imperfect point on a semiconductor pattern to be inspected is observed as an evaluation point (hereinafter referred to as EP) with the SEM, so that various geometrically dimensional values including the wiring width and the like the pattern has can be measured from an observed image and the maturity of the result of the pattern can be evaluated on the basis of the thus measured dimensional values.

In order for the EP to be imaged with high picture quality without positional shift, part or all of imaging points including an addressing point (AP), an auto-focus point (AF), an auto-stigmatism point (AST) and an auto-brightness/contrast control point (ABCC) are set and at individual imaging points, addressing, auto-focus adjustment, auto-stigmatism adjustment and auto-brightness/contrast adjustment, respectively, are conducted. As regards the amount of shift of imaging position in the addressing, matching between an SEM image at a known coordinate AP registered as a registry template in advance and an SEM image observed in actual imaging sequence (actual imaging template) is examined and an amount of positional shift in the matching is estimated as an imaging positional shift amount in addressing. The aforementioned EP, AP, AF, AST and ABCC are collectively called imaging points and the coordinates of points including part or all of the imaging points, the size/shape of an imaging area associated with an imaging point (simply, the imaging point size/shape), the imaging sequence of imaging points and the imaging condition and the registry template as well are managed in the form of an imaging recipe. Conventionally, the imaging recipe has been created manually by an SEM operator, imposing a laborious and time consuming job on the operator. Further, for determination of individual imaging points and registration of a registry template in an imaging recipe, a wafer must be imaged actually at low magnification and hence the creation of imaging recipe is a factor responsible for a degraded operating rate of SEM. In addition, as miniaturization of the pattern advances, followed by introduction of, for example, a technique of OPC (optical proximity correction), the number of EP's subject to evaluation increases extravagantly and the manual creation of the imaging recipe is prone to be impractical.

Under the circumstances, a semiconductor inspection system is disclosed in JP-A-2002-328015 in which an AP is determined on the basis of semiconductor circuit design data (hereinafter referred to as CAD (computer aided design) data) described in, for example, GDS2 format and data at the AP is cut out of the CAD data so as to be registered as the registry template (hereinafter, the template created by cutting the CAD data will be referred to as a CAD data template) in an imaging recipe. In the system, any actual wafer need not be imaged only for the sake of determination of the AP and registration of the registry template and improvements in the operating rate of SEM can be realized. Then, when an SEM image at the AP is acquired in actual imaging sequence (called an actual imaging template), the system functions to perform matching between the actual imaging template and the CAD data template, reregister an SEM image corresponding to a position of the CAD data template as an SEM image template in the imaging recipe and thereafter cause the reregistered SEM image template to be used for an addressing process. The system further has a function to automatically detect a characteristic part of pattern from the CAD data and register it as the AP.

SUMMARY OF THE INVENTION

In the prior art, problems as below are encountered in creating an imaging recipe used when a plurality of observation points on a specimen are imaged sequentially by using a scanning electron microscope.

Firstly, in order to inspect maturity or perfection of the result of a semiconductor pattern at an EP, an imaging recipe for imaging the EP must be prepared. As miniaturization of the semiconductor pattern advances, the number of EP's to be inspected increases, raising a problem that much labor and time are necessary for creation of the imaging recipe. As for automatic selection of AP coordinates, the aforementioned Patent Document gives a description "a characteristic pattern part is automatically detected" but fails to describe a specified method therefore and besides other information to be designated in the imaging recipe and regarding, for example, the necessity/needlessness of setting individual imaging points (AP, AF, AST, ABCC), the number of imaging points, the coordinates and size/shape of each imaging point, the imaging condition and the imaging sequence is designated pursuant to an existing manual, with the result that the automation rate of imaging recipe creation is very low and the SEM operator cannot be indebted to a large reduction of work time.

Further, in the actual imaging sequence, imaging or processing based on the prepared imaging recipe sometimes fails on account of a phenomenon unexpected during the creation of the imaging recipe (as an example, a failure in addressing attributable to defective formation of an actual pattern at an AP). Accordingly, there need a method of creating an imaging recipe which can prevent imaging or processing from failing in the presence of the aforementioned phenomenon and a relief method applicable to the case where imaging or processing fails even when the imaging recipe is created through the aforementioned creation method.

The present invention intends to provide a scanning electron microscope apparatus having the function to accurately and speedily create an imaging recipe whose performance is equivalent to or more excellent than that of an imaging recipe created manually on the basis of the unique know-how an SEM operator is stocked with and an imaging method using the apparatus.

According to the present invention, a scanning electron microscope apparatus has features described below and an imaging method uses the apparatus.

(1) In a recipe creation method, an imaging recipe for observation of an EP is created on the basis of CAD data representing design information of a pattern on a wafer as viewed in a low magnification field. Enumerated as imaging parameters are (a1) the number and (a2) coordinates and (a3) size/shape of imaging points (AP, AF, AST, ABCC) for observation of the EP, (a4) the imaging sequence (inclusive of imaging order of the EP and imaging points and electron beam vertically incident coordinates), (5a) imaging position changing method (stage shift, beam shift), (6a) imaging conditions (probe current, accelerating voltage, scan direction of electron beam and so on), and (a7) evaluation value or preferential order of the imaging sequence or the template. Then, output information includes part or all of the imaging parameters and the aforementioned imaging parameters and a template such as an AP template are registered in the imaging recipe.

(2) Available as input information are (b1) evaluation point information such as the coordinates of the EP, the size/shape and the imaging condition at the EP, (b2) design pattern information such as CAD data in the vicinity of the EP (inclusive of layer information), pattern extraction residual information of mask data, pattern line width information, the kind of wafer to be imaged, the process and material information for pattern and underlayer, (b3) processing parameters of the imaging recipe automatic creation engine such as search ranges of the imaging points (AP, AF, AST, ABCC), necessary condition for a selective factor index value the imaging point must satisfy (given by, for example, a threshold value of the index value), selective factor index preferential order (given by, for example, weighting among index values), a forbidden area prohibited from being selected as the imaging point, the estimative amount of discrepancy in shape between design pattern and actual pattern and apparatus conditions (stage shift range, stage shift/beam shift presumptive error), (b4) user's request specifications such as requested positioning accuracy of an imaging position for each imaging point, requested picture quality (requests for focus adjustment, stigmatism adjustment, brightness/contrast adjustment and contamination and a request for permissible electron beam incident angle at the EP as well) and requested imaging time and (b5) history information (such as information concerning succeeded (failed) imaging point in the past). Then, the input information includes any of the above pieces of information. In addition to the above pieces of information (b1) to (b5), the input information may include values or default values or settable ranges thereof of the output information (imaging parameters) (a1) to (a7) described in (1) above. Namely, a combination of arbitrary parameters from the above sets of (a1) to (a7) and (b1) to (b5) is set as the input information and a combination of arbitrary parameters of the above (a1) to (a7) is set as the output information.

(3) It is characteristic of the EP imaging sequence that making a decision as to whether imaging or processing at an arbitrary imaging point is successful or unsuccessful is accompanied. If the imaging or processing is determined to be unsuccessful in the success/failure decision, a relief process is taken which changes the imaging point or imaging sequence to make the imaging or processing successful.

(4) The templates at an evaluation point and at various imaging points determined in the recipe creation are registered in an imaging recipe. To this end, CAD data at the evaluation point or imaging points (CAD data template), modified CAD data resulting from a shape modification applied to the CAD data (modified CAD data template), a CAD image obtained by applying image quantization to the CAD data (CAD image template), a modified CAD image obtained by applying an arbitrary image process to the CAD image (modified CAD image template), an SEM image actually picked up at the evaluation point or imaging points (SEM image template) and a modified SEM image obtained by applying an arbitrary process to the SEM image (modified SEM image template inclusive of data converted to line segment data through line segment extraction) are selectively or totally registered in the imaging recipe in accordance with a matching scheme between an actual imaging template used for addressing an imaging position in the actual imaging sequence and a registry template.

According to the present invention, any operator having no special knowledge of the SEM can immediately be allowed to create a highly accurate imaging recipe without resort to a wafer and without depending on the difference in skill individual operators have, thereby attaining the following advantages.

(1) An imaging recipe can be created automatically at a high rate. The combination of input/output parameters can be set arbitrarily and desired output information can be obtained on the basis of a value or default value of a parameter which can be given as input information or a settable range thereof.

(2) Even in the event that imaging or processing based on the created imaging recipe fails on account of a phenomenon or inconvenience unexpected in the course of imaging recipe creation, a relief process can be taken which changes the imaging template or imaging sequence to make the imaging or processing successful.

(3) In calculation of a selective factor index, CAD data or a CAD image can be utilized selectively in accordance with the selective factor index to create a highly accurate imaging recipe within a short period of time.

(4) By calculating dense distribution information of line widths (line width map) from the CAD data, a proper image quantized width of less pattern shape collapse can be determined automatically. Further, by using a proper CAD image created with the image quantized width as input information in the calculation of an arbitrary selective factor index value, a good calculation accuracy of the selective factor index value can be obtained.

(5) For registration of the registry template, the aforementioned CAD data template, modified CAD data template, CAD image template or modified CAD image template is selectively or totally registered in the imaging recipe in accordance with the matching scheme between the actual image template plate and the registry template, so that speedup of the matching process and the high accuracy of matching can be achieved.

These and other objects, features and advantages of the invention will be apparent from the following more particular description of preferred embodiments of the invention, as illustrated in the accompanying drawings.

BRIEF DESCRIPTION OF THE DRAWINGS

FIG. 2A is a diagram for explaining irradiation of an electron beam on a semiconductor wafer.

FIG. 2B is a diagram showing states of individual pixels of an image in which electrons given off from the semiconductor wafer under irradiation of the electron beam are detected.

FIG. 4 is a flowchart showing the overall process.

FIG. 5 is a diagram of a list of input/output information.

FIG. 12A is a diagram showing procedures of creating modified CAD data, a CAD image and a modified CAD image from CAD data.

FIG. 12B is a diagram showing the state obtained by decomposing the CAD data interconnecting apexes by dotted lines to image quantized widths and imaging them.

FIG. 13A is a CAD diagram showing an exemplified setting of a forbidden area in consideration of a beam shift movable range.

FIG. 13B is a CAD diagram showing an exemplified setting of forbidden areas for suppression of deposition of contamination in consideration of plural EP's.

DESCRIPTION OF THE EMBODIMENTS

Embodiments of the present invention will now be described with reference to FIGS. 1 to 16B.

1. SEM 1.1 SEM Constituent Components

Figure 1:
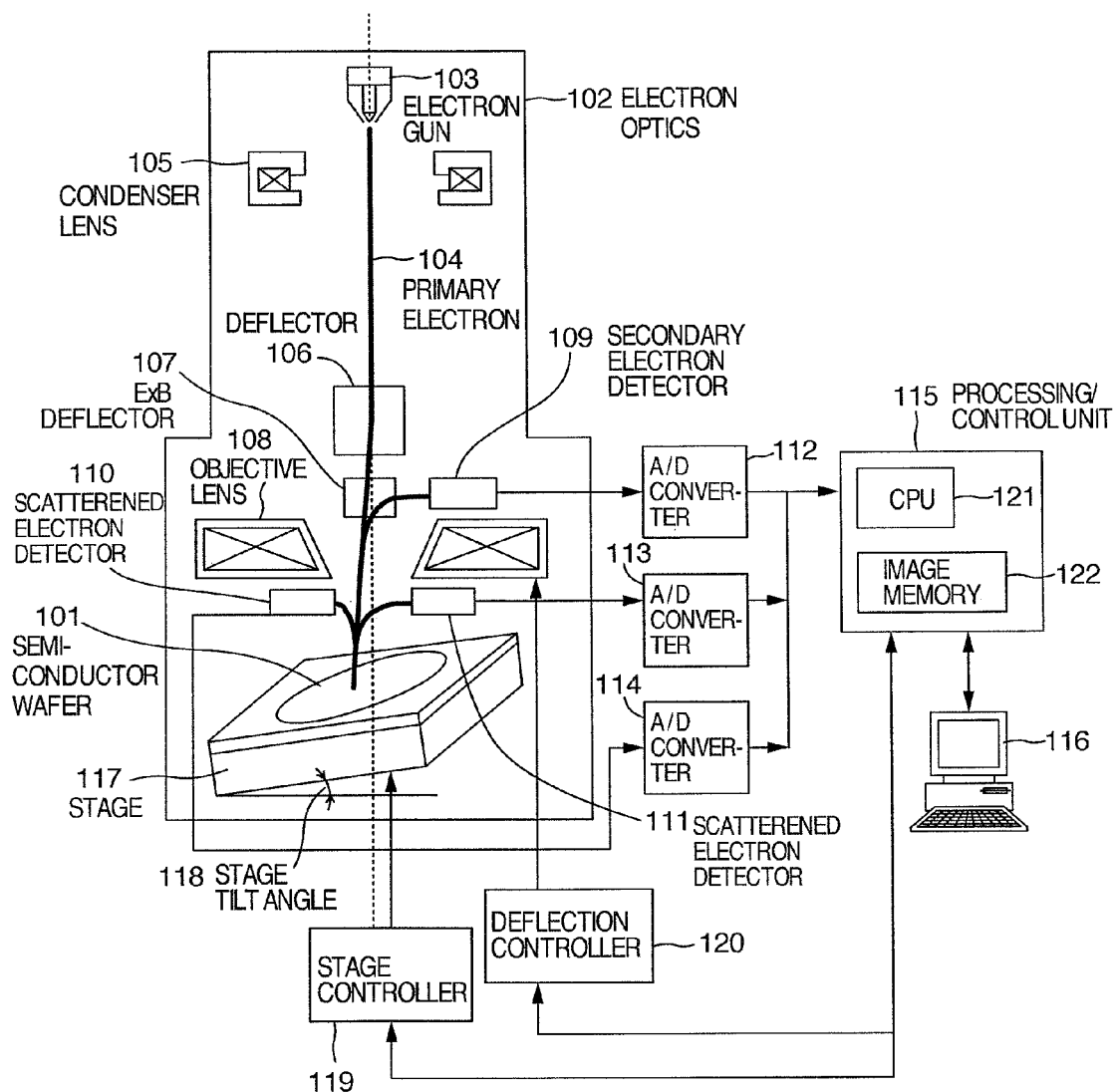
FIG. 1 is a schematic block diagram showing the construction of an SEM apparatus.

Referring first to FIG. 1, there is illustrated in block diagram form components constituting a scanning electron microscope (SEM) for acquiring a secondary electron image (SE image) or a backscattered electron image (BSE image) of a specimen in the embodiments of the invention. The SE image and the BSE image are generally termed an SEM image. An image acquired herein includes part or all of a top-down image of a measuring object observed in the vertical direction or of a tilt image of the object observed from a direction of arbitrary tilt angle.

An electron gun 103 emits an electron beam 104. The landing position of the electron beam and the aperture are controlled by means of a deflector 106 and an objective lens 108 such that the electron beam is focused and irradiated on an arbitrary position on a semiconductor wafer 101 representing a specimen mounted on a stage 117. Secondary electrons and backscattered electrons are given off from the semiconductor wafer 101 irradiated with the electron beam and secondary electrons whose trajectory is separated from that of the illuminating electron beam by means of an ExB deflector 107 are detected with a secondary electron detector 109. On the other hand, the backscattered electrons are detected with backscattered electron detectors 110 and 111. The backscattered electron detectors 110 and 111 are disposed in opposite directions. The secondary electrons detected by the secondary electron detector 109 and the backscattered electrons detected by the backscattered electron detectors 110 and 111 are converted into digital signals by means of A/D converters 112, 113 and 114 and are then stored in an image memory 122 so that they may be applied with image processing by means of a CPU 121 in accordance with purposes.

A method of producing an image from a signal amount of electrons given off from the semiconductor wafer 207 when the electron beam is scanned and irradiated on the semiconductor wafer will be described with reference to FIGS. 2A and 2B. For example, the electron beam is scanned and landed in x direction as indicated at 201 to 203 and in y direction as indicated at 204 to 206 in FIG. 2A. By changing the deflection direction of the electron beam, the scan direction can be changed. Locations on the semiconductor wafer indicated by G1 to G3 are irradiated with the electron beams 201 to 203 scanned in the x direction, respectively. Similarly, locations on the semiconductor wafer indicated by G4 to G6 are irradiated with the electron beams 204 to 206 scanned in the y direction, respectively. Amounts of electron signals emanating from the wafer at the G1 to G6 are indicative of values of intensities of illumination at pixels H1 to H6, respectively, in an image 209 shown in FIG. 2B (right below suffixes to G correspond to those to H, respectively). In FIG. 2B, a coordinate system for defining x and y directions on the image is designated by 208.

Designated at 115 in FIG. 1 is a computer system which performs processing/control, such as transmission of control signals to a stage controller 119 and a deflection controller 120 or application of various kinds of image processing to an image picked up at an arbitrary imaging point on the semiconductor wafer 101, in order to photograph the imaging point on the basis of an imaging recipe. The imaging point referred to herein includes part or all of points each for addressing, auto-focus, auto-stigmatism or auto-brightness/contrast and an evaluation point. The processor/controller 115 is connected to a display 116 and provided with a GUI (graphic user interface) for displaying images to the user. The XY stage 117 is adapted to move the semiconductor wafer 101 to enable an image at an arbitrary position on the semiconductor wafer to be imaged. Changing the observation position by means of the XY stage 117 is called stage shift and changing the observation position by deflecting the electron beam with the deflector 106 is called beam shift. Speaking of general properties, the stage shift provides a wide movable range but has a low accuracy of positioning the imaging position and contrarily, the beam shift provides a narrow movable range but has a high accuracy of positioning the imaging position.

In FIG. 1, the embodiment is described as having the two backscattered electron detectors but the number of the backscattered electron detectors can be decreased or increased.

The computer system 115 functions to create an imaging recipe through a method to be described later and perform imaging by controlling the SEM apparatus on the basis of the imaging recipe but part or all of the processing/control as above can be assigned to a plurality of processing terminals and executed thereby, as will be detailed later with reference to FIGS. 16A and 16B.

Available as methods of acquiring a tilt image by observing a measuring object from a direction making an arbitrary tilt angle are (1) a method in which a tilt image is picked up by deflecting an electron beam illuminating through an electron optics so as to tilt the irradiation or landing angle of the electron beam (for example, JP-A-2000-348658), (2) a method in which the stage 117 itself for moving the semiconductor wafer is tilted (in FIG. 1, the stage is tilted through a tilt angle 118) and (3) a method in which the electron optics per se is tilted mechanically.

1. 2 SEM Imaging Sequence

Figure 3B:
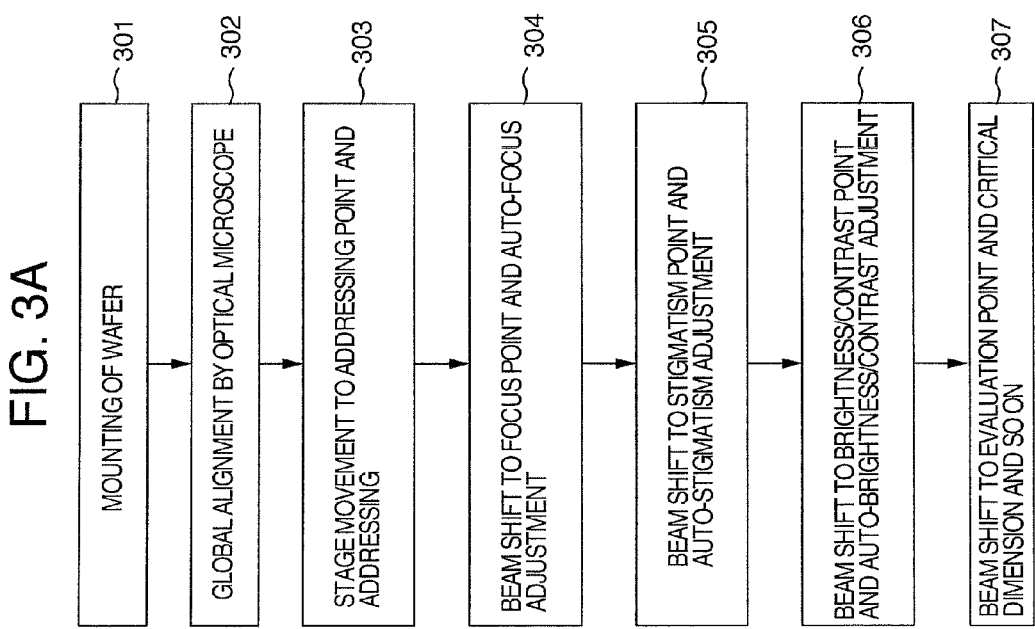
FIG. 3B is a diagram showing an example of template positions on a low magnification image.
Figure 3A:
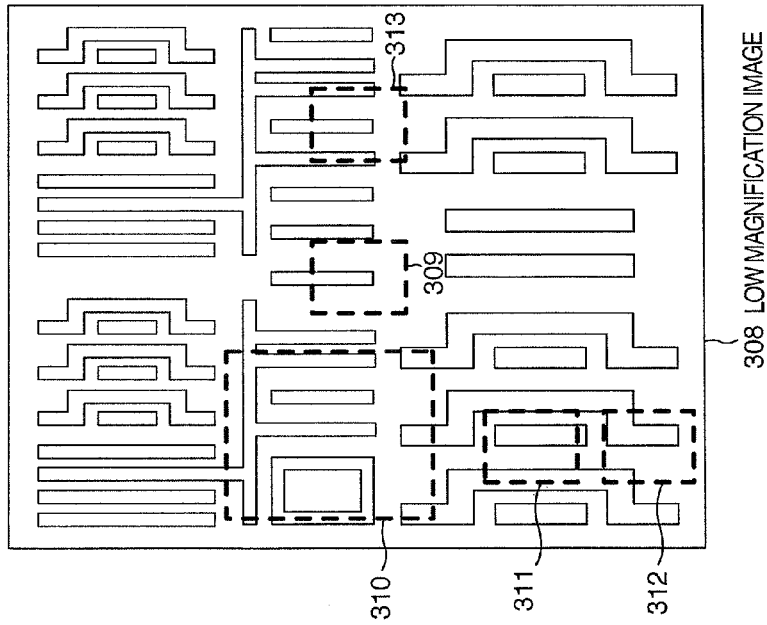
FIG. 3A is a flowchart showing the imaging sequence.

Turning to FIG. 3A, typical imaging sequence for observing an arbitrary evaluation point (EP) will be described. In the imaging sequence, an imaging point, an imaging order and an imaging condition are designated by an imaging recipe.

Firstly, in step 301 in FIG. 3A, a semiconductor wafer representing a specimen is mounted to the stage 117 of SEM apparatus. In step 302, by observing a global alignment mark on the wafer with an optical microscope, for example, the wafer is corrected for its origin shift and its rotation.

In step 303, the stage 117 is moved on the basis of control and processing by the processor/controller 115 in order that an imaging position is moved to an addressing point (AP), followed by imaging, parameters for addressing are determined and addressing is carried out on the basis of the determined parameters. To give an additional explanation of the AP, it will be appreciated that if, in the course of observation of an EP, the EP is managed for direct observation by way of stage shift, there is a danger of a large shift of the imaging point attributable to the positioning accuracy of the stage.

Therefore, an AP is observed to which coordinate values of an imaging point and its template (a pattern of the imaging point) are once designated in advance for positioning. The template is registered in the imaging recipe and will therefore be called a registry template hereinafter. The AP is selected from the vicinity of the EP (within a movable range based on the beam shift at the most). As compared to the EP, the AP is generally observed in a lower magnification field of view and therefore, even in the presence of a slight shift of imaging position, a dangerous deficiency that the pattern to be imaged as a whole is outside the field of view can be mitigated. Then, by performing matching between the registry template of AP registered in advance and an actually photographed SEM image of the AP (actual image template), an amount of positional shift of the imaging point at the AP can be estimated. Since coordinate values of the AP and EP are known, a relative displacement amount between the AP and the EP can be determined and besides, the positional shift amount of the imaging point at the AP can be estimated through the aforementioned matching, thereby ensuring that the relative displacement amount by which an actual movement is to be done from the AP imaging position to the EP can be known by subtracting the positional shift amount from the relative displacement amount. Accordingly, by making a movement by the relative displacement amount through the beam shift of high positioning accuracy, the EP can be imaged with high coordinate accuracies.

Accordingly, the AP to be registered preferably satisfies conditions (1) the registry AP is a pattern existing at a distance from the EP reachable through beam shift movement (and besides, the range (field of view: FOV) at the time of imaging the AP is sometimes so conditioned as not to contain the FOV at the time of imaging the EP to suppress generation of contamination at the EP, (2) the imaging magnification for the AP is lower than that for the EP in consideration of the positioning accuracy of the stage and (3) the registry AP is characteristic of a pattern shape or a brightness pattern and is easy to assure matching between the registry temple and the actually imaged temple. Conventionally, the SEM operator manually makes a decision as to which location is to be selected as the AP but advantageously, in the present invention, the aforementioned conditions are evaluated inside the system to automatically select a good or convenient AP and determine the imaging sequence.

The registry template at the AP can be a CAD image or an SEM image but in a conceivable variation, to avoid the imaging operation from being done only for the purpose of registering the imaging template as disclosed in JP-A-2002-328015, the imaging template at the AP may once be registered in the form of a CAD data template and an SEM image of the AP obtained by actual imaging may be reregistered as an SEM image template.

A complementary description will be given of the aforementioned AP selection range or FOV. Generally, the electron beam vertically incident coordinates are set at the center coordinates of the EP and so, the selectable range of the AP coincides at the most with the beam shift movable range centered on the EP. But when the electron beam vertically incident coordinates differ from the center coordinates of the EP, a selectable range coincides with a beam shift movable range from the electron beam vertically incident coordinates. Depending on a permissible electron beam incident angle required of the imaging point, the search range from the electron beam vertically incident coordinates sometimes becomes smaller than the beam shift movable range. This holds true for other templates. In the following description, unless particularly noticed, the electron beam vertically incident coordinates will be described as being identical with the center coordinates of the EP in the case of imaging a single EP but as mentioned previously, the present invention is not limited thereto. Details of the electron beam vertically incident coordinates will be described later with reference to FIGS. 14A to 14C.

Next, in step 304, the imaging position is moved to an auto-focus point (AF) through beam shift on the basis of control/processing by the processor/controller 115, followed by execution of imaging, parameters for auto-focus adjustment are determined and an auto-focus adjustment is made on the basis of the settled parameters. The AF will be described additionally herein. With the aim of acquiring a clear image, an auto-focus is made during imaging but when the electron beam is irradiated on the specimen for a long time, contaminative substances are deposited on the specimen (contamination). Therefore, to restrain deposition of contamination at the EP, coordinates of the vicinity of the EP are once observed as the AF to obtain parameters of auto-focus and the EP is then observed on the basis of the thus obtained parameters.

For the reasons as above, the AF to be registered preferably satisfies conditions (1) the registry AF has a pattern existing at a distance from the AP and EP reachable through beam shift movement and besides an FOV during AF imaging does not include an FOV during EP imaging, (2) the imaging magnification for the AF is comparable to that for the EP (but, this holds true when the AF is for the EP. In the case of the AF for the AP, the AF is imaged at the imaging magnification comparable to that for the AP. This stands for AST and ABCC to be described later.) and (3) the registry AF has a pattern shape easy to undergo auto-focus (prone to facilitate detection of an image blur due to a defocus). According to the present invention, like the AP, the aforementioned conditions are evaluated for the sake of AF selection inside the system, permitting excellent automatic AF selection.

Next, in step 305, the imaging position is moved to an auto-stigmatism point (AST) through beam shift on the basis of control/processing by the processor/controller 115, followed by execution of imaging, parameters for auto-stigmatism adjustment are determined and an auto-stigmatism adjustment is made on the basis of the determined parameters. The AST will be described additionally herein. With the aim of acquiring an image devoid of distortion, a correction for astigmatic aberration is made during imaging but when the electron beam is irradiated on the specimen for a long time, as in the case of the AF, contaminative substances are deposited on the specimen (contamination). Therefore, to restrain deposition of contamination at the EP, coordinates of the vicinity of the EP are once observed as the AST to obtain parameters of auto-astigmatism correction and the EP is then observed on the basis of the parameters.

For the reasons as above, the AST to be registered preferably satisfies conditions (1) the registry AST has a pattern existing at a distance from the AP and EP reachable through beam shift movement and besides an FOV during AST imaging does not include an FOV during EP imaging, (2) the imaging magnification for the AST is comparable to that for the EP and (3) the registry AST has a pattern shape easy to undergo the astigmatism correction (prone to facilitate detection of an image blur due to an astigmatic aberration).

According to the present embodiment, like the AP, the aforementioned conditions are evaluated for the sake of AST selection inside the system, permitting excellent automatic AST selection.

Subsequently, in step 306, the imaging position is moved to an auto-brightness/contrast point (ABCC) through beam shift on the basis of control/processing by the processor/controller 115, imaging is executed, parameters for auto-brightness/contrast adjustment are determined and an auto-brightness/contrast adjustment is made on the basis of the determined parameters. The ABCC will be described additionally herein. With the aim of acquiring a clear image having proper brightness value and contrast, a parameter such as voltage of a photomultiplier in the secondary electron detector 109, for example, is adjusted so that setting can be made to make, for example, the highest part and the lowest part of an image signal fully contrasted or so but as in the case of the AF, when the electron beam is irradiated on the specimen for a long time, contaminative substances are deposited on the specimen. Therefore, to restrain deposition of contamination at the EP, coordinates of the vicinity of the EP are once observed as the ABCC to obtain parameters for brightness/contrast control and the EP is then observed on the basis of the parameters.

For the reasons as above, the ABCC to be registered preferably satisfies conditions (1) the registry ABCC has a pattern existing at a distance from the AP and EP reachable through beam shift movement and besides an FOV during ABCC imaging does not include an FOV during EP imaging, (2) the imaging magnification for the ABCC is comparable to that for the EP and (3) the ABCC has a pattern similar to that at the critical dimension point in order that the brightness/contrast of an image picked up at the critical dimension point by using the parameters adjusted at the ABCC can be excellent. According to the present invention, like the AP, the aforementioned conditions are evaluated for the sake of ABCC selection inside the system, permitting excellent automatic ABCC selection.

In an alternative, imaging the AP, AF, AST and ABCC in the steps 303, 304, 305 and 306, respectively, may sometime be omitted partly or totally, the order of 303, 304, 305 and 306 may be exchanged arbitrarily or the coordinates of the respective AP, AF, AST and ABCC may partly overlap (for example, the auto-focus and auto-stigmatism may be carried out at the same coordinates).

Finally, in step 307, the imaging point is moved to the EP through beam shift, followed by imaging, and under set critical dimension conditions, for example, critical dimension of the pattern is measured. Even at the EP, matching is sometimes performed between the picked-up SEM image and the registry template corresponding to the EP position and registered in advance in the imaging recipe and a measured positional shift is detected. The imaging recipe is written with coordinates of the aforementioned imaging points (EP, AP, AF, AST, ABCC), the imaging sequence and information such as imaging conditions and the SEM observes the EP on the basis of the imaging recipe. Examples of template positions of EP309, AP310, AF311, AST312 and ABCC313 on a low magnification image 308 are illustrated at dotted line blocks in FIG. 3B.

The present embodiment concerns the method for automatic creation of the imaging recipe. By automating the imaging recipe creation conventionally carried out manually, time required for recipe creation can be shortened to promote the total throughput inclusive of preparation for imaging the SEM exhibits. Since, in creating the imaging recipe, the imaging recipe creation is based on design layout information of a semiconductor pattern managed as CAD (computer aided design) data (CAD data) instead of a low magnification image of an actual wafer, creation work can be executed in an off-line fashion, leading to improvements in operating rate of the SEM.

2. Imaging Recipe Automatic Creation Function
2. 1 Input/Output Information

The imaging recipe has been described with reference to FIGS. 3A and 3B by way of a set of EP, AP, AF, AST and ABCC exemplifying information to be registered in the imaging recipe. Input/output information used in the recipe automatic creation method and apparatus according to the invention is listed in FIG. 5. In the figure, pieces of information 502 to 519 positioned at ends of arrows (see an explanatory note on arrow at 537) extending to an imaging recipe automatic creation engine 501 indicate pieces of input information to the engine 501. Pieces of information 521 to 536 positioned at ends of links (see an explanatory note on link at 538) connecting to the engine 501 by way of black dots can be either input information or output information to or from the engine 501.

In other words, the engine 501 features that it can calculate an arbitrary information combination out of pieces of information 502 to 519 and pieces of information 521 to 536 as input information and an arbitrary information combination out of pieces of information 521 to 536 as output information and can deliver the input information and output information. Further, the engine can exclude as unwanted information an arbitrary information combination out of pieces of information 502 to 519 and an arbitrary information combination out of pieces of information 521 to 536 from any of the input information and output information. In connection with a method of selecting an arbitrary combination from piece of information 502 to 519 and pieces of information 521 to 536 and providing the selected combination as input information and a method of causing the engine 501 to calculate output information, there are two variations to be described below and the variations can be used selectively for the input information and output information.

(1) As regards arbitrary information selected as input information, the user designates a fixed value of the input information or sets a default value prepared in advance in the database 536, for example, as the input information. On the presupposition of the fixed value or the default value, the engine 501 calculates an arbitrary output value. The output information is allowed to contain the input information. In this case, the engine 501 recalculates an appropriate value of the input information on the basis of the inputted input information and delivers the recalculated value.

(2) As regards arbitrary information selected as input information, the user sets a range of values the input information can take or sets a default value in a range of values the input information can take prepared in advance in the database 536. On the presumption that the input information can change within the range, the engine 501 calculates arbitrary output information. The output information can include the input information. In this case, within a range of values the inputted input information can take, the engine 501 calculates an appropriate value of the input information and delivers it.

Next, details of the input information pieces 502 to 519 and the input/output information pieces 521 to 536 the engine 501 receives/delivers will be described.

2. 1. 1 Input Information

Available as information 502 of evaluation point are coordinates 503 of evaluation point EP [p], size/shape 504 (of an imaging area) and imaging conditions 505 (probe current, accelerating voltage, scan direction of electron beam and so on), where arrange number p indicates ID's of a plurality of evaluation points set on a chip located on the wafer (p=1 to Np, Np≥1). Generally, the evaluation point is in the form of a square area or rectangular area but other arbitrary shapes can be set as an imaging area.

Enumerated as the design pattern information 506 are CAD (computer aided design) data 507 in the vicinity of an EP, pattern extraction residue information 508 of mask data, line width information 509 of pattern (or minimum line width information) and information 510 concerning the kind of a wafer to be imaged, the process and the material of pattern or underlayer. The CAD data is design information of semiconductor pattern described in, for example, GDS2 format and is formulated by, for example, an arrangement of apex coordinates (x, y) of a contour of the design pattern. The CAD data also includes layer information, so that data can be processed layer by layer or a plurality of arbitrary layers can be processed in a superimposed fashion.

The extraction residue information 508 is information indicative of an area at which the resist film is removed after exposure/development or a left-behind area (that is, an area serving as an underlayer or an area where a gate wiring pattern is formed). Alternatively, however, the extraction residue information 508 and pattern width information 509 can be calculated as necessary from the CAD data 507 inside the imaging recipe automatic creation engine 501. Broadly or universally, CAD data can include, as design information, the CAD data 507, the extraction residue information 508, the pattern line width information 509 and the kind/process/material information 510. Using the information 508 to 510 as input information or calculating these pieces of information in the imaging recipe automatic creation engine 501 is efficient in points as below.

More particularly, various kinds of actual imaging templates picked up in the actual imaging sequence are SEM images but in the imaging recipe automatic creation engine 501, imaging points suitable for the templates are selected on the basis of the CAD data. Therefore, with a view to filling the discrepancy between the actual SEM image and the CAD data, a CAD image more resembling an actual SEM image is created by taking the extraction residue information 508 and kind/process/material information 510 into account, thereby ensuring that the accuracy of a selection process can be promoted in, for example, evaluation of peculiarity of imaging point to be described later.

Further, with the line width information 509 and the kind/process/material information 510 used, proneness of a pattern to deformation attributable to the line width, kind, process and material (for example, proneness to deformation caused by fluctuation in light-exposure parameter) can be considered additionally as a selective factor index value and such a process as selecting an imaging point inclusive of a pattern as hardly deformable as possible can be permitted. Furthermore, as will be described later, the line width information 509 can be used as input information necessary for calculation of a selective factor index value inside the imaging recipe automatic creation engine 501 and when creating a CAD image, is efficient for determination of an image quantizing width (nm/pixel) necessary for creation of the CAD image from a CAD data.

Enumerated as the processing parameter 511 are selective process parameter 512, shape discrepancy estimative amount 513 between a design pattern and an actual pattern and SEM apparatus condition 514. The selection process parameter 512 defines part or all of parameters of a search range of an arbitrary imaging point (for example, a range within which movement from the EP is possible through the beam shift), a necessary condition of selective factor index value to be described later (threshold value), a selective factor index preferential order (weight) and a forbidden area in imaging point selection (for example, with the aim of suppressing contamination, selection of an imaging point from an EP area and the vicinity x (pixel) of the EP area is prohibited.)

The shape discrepancy estimative amount 513 between a design pattern and an actual pattern defines an amount of deformation an actual pattern shape exhibits in relation to a design pattern shape on account of optical proximity effect (OPE) and fluctuation of the light-exposure condition. For example, in the case of a line pattern, the shape discrepancy estimative amount 513 corresponds to an amount of shrinkage and an amount of rounding at the line end. By reflecting the shape discrepancy estimative amount 513 on the evaluation of a pattern shape associated with an imaging point based on the design data, failure in pattern shape evaluation and imaging point selection concomitant with the deformation amount can be avoided. The SEM apparatus condition 514 defines parameters indicative of characteristics of the SEM apparatus represented by the movable range through beam shift and the stage shift/beam shift estimative positioning error. With the beam shift movable range inputted as input information, it can be decided whether movement between arbitrary imaging points through beam shift is possible, offering efficiency in determination of the imaging sequence and imaging position change method (stage shift or beam shift).

Also, with the stage shift/beam shift estimative error used as input information, a shift of field of view possibly occurring at an imaging point picked up after the imaging position change through the stage shift/beam shift (for example, 1007 in FIG. 10B) can be anticipated. In selecting various kinds of imaging points, by making an evaluation as to whether a pattern suitable for an intended process is included in an area 1008 exclusive of a pattern that is caused to be outside the field of view on account of the shift of field of view as shown in FIG. 10B, selection of an imaging point invulnerable to the influence of the view field shift can be assured.

Enumerated as the user request specifications 515 are requested positioning accuracy 516 at the EP, requested picture quality 517 and requested imaging time 518. The requested picture quality 517 includes a request for focus, stigmatism and brightness/contrast necessary to acquire a clear image, a request for contamination generation suppression and a request for permissible electron beam incident angles at an evaluation point and various imaging points. Details of the permissible electron beam incident angle will be described later with reference to FIGS. 14A to 14C. Necessity/needlessness of setting of various imaging points, the coordinates, size/shape and imaging sequence (inclusive of imaging order and electron bema vertically incident coordinates) of various imaging points and the imaging position change method are so determined as to satisfy the requested specifications. Especially, to meet the requested positioning accuracy 516, the necessity/needlessness of setting an AP, the coordinates thereof, size/shape at the AP, the imaging sequence at the AP and the imaging position change method are adjusted, to meet the requested picture quality 517, the necessity/needlessness of setting AF, AST or ABCC, its coordinates, its size/shape, its imaging sequence and the imaging position change method are adjusted and to meet the requested imaging time 518, the number of imaging operations at various imaging points, their size/shape and the imaging position change method are adjusted.

The history information 519 is a library of results and knowledge of old processes and the information is consulted by the imaging recipe automatic creation engine 501 to permit better imaging recipe creation. For example, by managing, as history information, information of an imaging point or imaging sequence which failed to be imaged or processed in the past, a process can be allowed which does not create an imaging recipe resembling an old unsuccessful imaging recipe. Conversely, a process can be allowed which upgrades the evaluation value or preferential order in an imaging recipe resembling an imaging point or imaging sequence which succeeded in imaging or processing in the past.

2. 1. 2 Input Information or Output Information

Enumerated as the imaging point coordinates 521 are coordinates of AP, AF, AST and ABCC designated by reference numerals 522 to 525, respectively. These imaging points are set in association with individual evaluation points EP[p], where p=1 to Np, Np≥1, and a plurality of imaging points for arbitrary processing can be set (for example, addressing is made at or from two AP's and then an EP is imaged). The above condition is expressed by AP[p][q], AF[p][q], AST[p][q] and ABCC[p][q] (q=1 to Nq, Nq≥1). The arrangement number p indicates ID's of a plurality of evaluation points set on a chip located on a wafer and the arrangement number q indicates ID's of templates for individual processes routed when an arbitrary evaluation point EP[p] is observed (the imaging points AP, AF, AST and ABCC are handled as one set (the imaging order and the presence or absence of imaging at each imaging point are arbitrary) and the arrangement number q indicates an ID of the set). But, as will be described later, arbitrary imaging templates can be shared by different EP's (for example, for EP[p1] and EP[p2] (p1≠p2), AP[p1][q1] and AP[p2][q2] are equal). In addition, unnecessary AP[p][q], AF[p][q], AST[p][q] and ABCC[p][q] can be deleted arbitrarily from the imaging sequence.

Enumerated as the size/shape 526 of imaging area are sizes and shapes at AP[p][q], AF[p][q], AST[p][q] and ABCC[p][q] designated by reference numerals 527 to 530, respectively. Generally, the shape at an imaging point is a square area like at the EP but for inclusion of pattern areas effective for various processes or exclusion of areas liable to be inconvenient, it can be a rectangular area or other arbitrary shapes. The size/shape can be applied as input information or can be optimized inside the imaging recipe automatic creation engine 501 so as to be outputted. Further, a constraint condition can be imposed on the size/shape of some imaging points (for example, the shape is restricted to a rectangular area and the size is selected from the range of  to  (nm)) and the size/shape of some imaging points or the size/shape of other imaging points can be outputted.

The imaging sequence 531 designates which order the aforementioned EP]p], AP[p][q], AF[p][q], AST[p][q] and ABCC[p][q] are imaged or subjected to various processes in. The imaging position change method 532 designates a method for changing the field of view in individual imaging steps of the imaging sequence (stage shift or beam shift).

The imaging condition 533 includes probe current, accelerating voltage and scan direction of the electron beam. The registry template 535 includes templates of imaging range (FOV) cut at the EP[p], AP[p][q], AF[p][q[, AST[p][q[ and ABCC[p][q] and in consideration of a shift of field of view, the template can be cut in a slightly larger dimension as necessary. Not all templates at the EP[p], AP[p][q], AF[p][q], AST[p][q] and ABCC[p][q] are required to be registered but the template may be registered as criteria of addressing and various processes only for an imaging point which needs imaging parameters and a template as well.

As for registry template 535, one or more can be selected from six data formats of CAD data at an imaging point, a CAD image obtained by image-quantizing the CAD data, CAD data applied with a predetermined process (to be described later), a CAD image applied with a predetermined process (to be described later), an SEM image and an SEM image applied with a predetermined process (inclusive of an instance of conversion to line segment information) and can be registered as temples. For example, in addressing, the data format of an effective registry temple depends on a matching scheme between an actual image template used for addressing of an imaging point in the actual imaging sequence and a registry template and therefore from the standpoint of speedup of matching process and high accuracy of matching, the aforementioned selection of data format is efficient.

The database 536 is adapted to save/manage part or all of the information pieces 502 to 535 described previously. As for the aforementioned information, information on time series or distributed over different SEM apparatuses can be shared for handling. The imaging recipe automatic creation engine 501 can read arbitrary information from the database 536 as necessary and reflect it on various kinds of processes. In determining values or ranges of the various kinds of input information 502 to 535, old parameters saved in the database 536 can be consulted and besides, default values of the aforementioned values or ranges can be saved in respect of individual kinds or fabrication steps, for example.

Among the above items, the imaging point or imaging sequence evaluation value or preferential order 534 will be described in greater detail. The automatic recipe creation method in the present invention features making a decision as to success/failure of imaging or process applied to an arbitrary imaging point. The method also features a relief process carried out, when the imaging or process is determined to be unsuccessful in the success/failure decision, to change the imaging point and imaging sequence for the purpose of making the imaging or processing successful. Accordingly, according to a feature of the invention, during the imaging recipe creation, a plurality of candidates for imaging sequence 531 applied to change the aforementioned imaging point coordinates 521, imaging point size/shape 526, imaging position change method 532 and imaging condition 533 are calculated and besides, evaluation values or preferential order of these candidates are calculated. In the actual imaging sequence, imaging or processing is executed in accordance with an imaging point or imaging sequence having a higher evaluation value or preferential order and when the imaging or processing is determined to be unsuccessful, the imaging template or imaging sequence is changed on the basis of the evaluation value or preferential order.

Figure 6A:
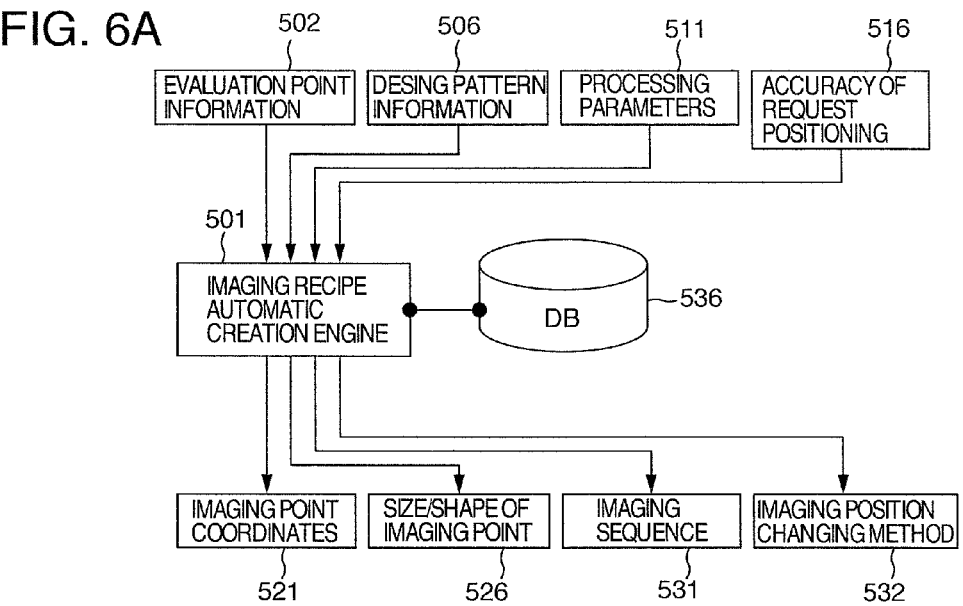
FIG. 6A is a block diagram showing an example of a combination of generally described input/output information.
Figure 6B:
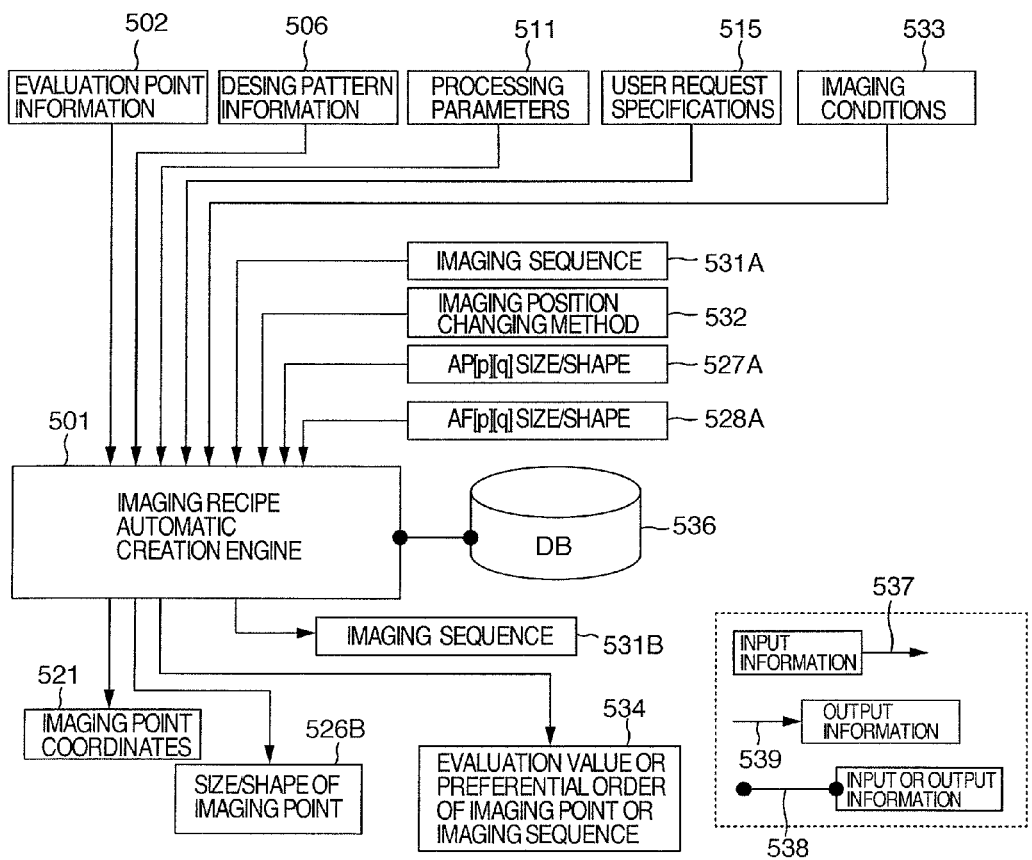
FIG. 6B is a block diagram showing another example of a combination of generally described input/output information.

Two examples of typified input/output combinations are extracted from the list of input/output information generally described in FIG. 5 are illustrated in FIGS. 6A and 6B. For example, in the example shown in FIG. 6A, the imaging recipe automatic creation engine 501 provides, as input information, evaluation point information 502, design pattern information 506, process parameter 511 and requested positioning accuracy 516 and estimates, for output information, imaging point coordinates 521, imaging point size/shape 526, imaging sequence 531 and imaging position change method 532. In this case, only the positioning accuracy 516 is designated as the user requested specifications 515 and the imaging condition 533 is eliminated from both the input information and output information. The example illustrated in FIG. 6B differs from the FIG. 6A example in that part of imaging sequence 531A, imaging position change method 532, AP[p][q] size/shape 527A and AF[p][q] size/shape 528A are used as input information and residual imaging sequence 531B and residual imaging point size/shape 526B are used as output information.

As a concrete example, in the input information, a condition "An EP is imaged after addressing at an AP. The number of AP's is two at the most. An auto-focus process is necessarily carried out at an AF before imaging the EP." is set to the part of imaging sequence 531A, a condition "Only for the first AP, the field of view is moved through stage shift and view field movements to the remaining templates are all done through beam shift." is set to the imaging position change method 532, a condition "A size of a proper value within a range of 3 to 5 μm is set to the first AP and the AP's are all square areas." is set to the AP[p][q] size/shape 527A and a condition "The AF size before EP imaging is the same as the EP size." is set to the AF[p][q] size/shape 528B. In the output information, as the residual imaging sequence 531B and residual imaging point size/shape 526B, "A particular size of the first AP (within the range of 3 to 5 μm as above) and, if setting is necessary, a size of the second AP and sizes/shapes of AST and ABCCC" is estimated. If necessary, for relief in the event of a failure in imaging or processing, a plurality of imaging points and a plurality of imaging sequences are outputted (as the imaging template changes over, the imaging sequence ought to be changed). Further, evaluation value or preferential order of imaging point or imaging sequence 534 is also outputted.

The input information as above can be designated directly by the user or can be inputted by reading a default setting saved in, for example, the database 536. Many pieces of the aforementioned information given to the input information can be information effective to imaging recipe creation but information permitted to be inputted or uncertain information differs depending on, for example, the kind, the production process and the SEM apparatus. Some users will want to save the time and labor of inputting. According to the invention, combinations of the input/output information pieces can be set at will.

2. 2 Imaging Sequence (Basic Sequence and Division of Imaging Point)

Referring to FIGS. 7A to 7G, examples of setting of imaging point disposition and imaging sequence in low magnification field of views 701a to 701g will be described. In each figure, a dotted block indicates an imaging range (FVO) of each imaging point registered in the imaging recipe, a solid arrow indicates a stage shift, a dotted arrow indicates a beam shift and encircled numerals 1 to 15 on the solid and dotted arrows indicate the imaging order. The following description will be given by making reference to FIGS. 7A to 7G sequentially.

Figure 7A:
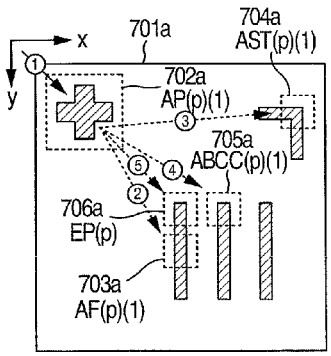
FIG. 7A is a diagram showing the imaging sequence for imaging an arbitrary p-th evaluation point EP.

Especially illustrated in FIG. 7A is an example of imaging sequence for imaging an arbitrary p-th evaluation point EP]p] (706a). Individual parameters (coordinates, size/shape, imaging condition and so on) of EP[p] (706a), AP[p][1] (702a), AF[p][1] (703a), AST[p][1] (704a) and ABCC[p][1] (705a) are designated as imaging points in the imaging recipe and besides, in connection with the EP[p] (706a) and AP[p][1] (702a), registry templates are saved.

Firstly, movement to the AP[p][1] (702a) is effected through stage shift (1 in the figure) and an imaged actual template is matched with a registry template at the AP[p][1] to estimate (address) image shift amounts in x and y directions. Next, movement to the AF[p][1] (703a) through beam shift is effected (2 in the figure) to perform an auto-focus adjustment. The beam shift amount equals a difference obtained by subtracting the imaging shift amount from the amount of displacement from the AP[p][1] coordinates to the AF[p][1] coordinates. Subsequent movement to respective imaging templates through beam shift is corrected by the imaging shift amount as in the case of the movement to the AF. Thereafter, movement to the AST[p][1] (704a) is effected through beam shift (3 in the figure) to perform an auto-stigmatism adjustment. Then, movement to the ABCC [p][1] (705a) is effected through beam shift (4 in the figure) to perform an auto-brightness/contrast adjustment.

In this example, for the AF, AST and ABCCC, any registry template is not saved in the imaging recipe but the registry template may be saved also in connection with the AF, AST and ABCC and by making matching with an actually imaged actual imaging template, whether correct movement to the registered imaging point is successful can be decided or a criterion of process can be provided. In the process criterion, it is preferable that for the AF, the focus adjustment is so made as to make contrast of wiring edge high but for preventing noise from being erroneously emphasized as an edge, an edge position is discriminated from the registry template and an adjustment is made such that contrast of the wiring edge can be emphasized correctly. Finally, movement to the EP[p] (706a) is effected through beam shift (5 in the figure) and imaging is carried out.

It is to be additionally noted that the arrows indicative of beam shift in the 2nd to 5-th imaging operations in FIG. 7A all originate from the AP[p][1] (702a) to indicate that the field of view is moved to the individual imaging points on the basis of the addressed coordinate value at the AP[p][1]. In other words, for example, the AF[p][1] (703a) directed by arrow 2 is observed and thereafter the view field movement to the next AST[p][1] (704a) is completed by making the beam shift from the AF[p][1] (703a) by a displacement of AF[p][1] (703a)-AST[p][1] (704a). Advantageously, in the present invention, the imaging sequence as above can be determined automatically.

Although setting is not exemplified in FIG. 7A, for the sake of performing good addressing at, for example, the AP[p][1] (702a), an AF for the AP[p][1] (702a) can be set and an auto-focus adjustment can be made at the AF before imaging the AP[p][1] (702a). To inscribe imaging points in this case, the AF for AP[p][1] (702a) is indicated by AF[p][1] and the AP[p][1], AF[p][1], AST[p][1] and ABCC[p][1] shown in FIG. 7A are rewritten to AP[p][2], AF[p][2], AST[p][2] and ABCC [p][2], respectively.

Figure 7B:
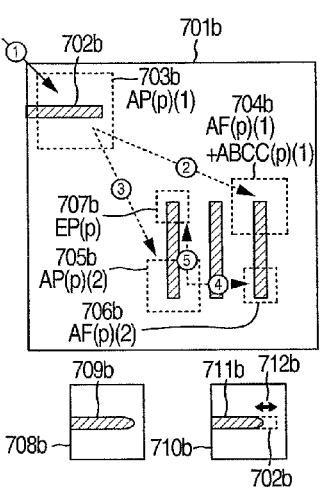
FIG. 7B is a diagram showing the imaging sequence when two AP's are set.

In FIG. 7B, an example of setting two AP's is illustrated. Stage/beam shift and addressing are carried out in the same way as that in FIG. 7A and will not be descried herein. In FIG. 7B, AP[p][1] (703a) is selected as the initial AP but in the AP[p][1], only a wiring pattern 702b elongated in x direction exists. Actual image templates 708b and 710b both show cases which will possibly occur when coordinates of AP[p][1] (703b) are observed with the SEM in the actual imaging sequence. In the case of observed image 708b, an actually formed wiring pattern 709b substantially equally positioned to the corresponding design data 702b with the exception that the line end on the right end side is rounded. In the case of observed image 710b, however, an actual wiring pattern 711b is largely contracted, as compared to the design data 702b complemented by dotted line in the figure, owing to fluctuations in the production process parameters (the gap is indicated by arrow 712b).

When, in the object as above, the positional shift amount estimation based on matching between registry template 703b and actual image template 710b is conducted, matching is done with a shift corresponding to the gap 712b and even if no positional shift amount exists in effect, there is a deficiency that a positional shift amount corresponding to the gap 712b is detected erroneously. In other words, because of the shortage of the edge in x direction the pattern has in the AP[p][1] (703b), the accuracy of addressing using the AP[p][1] (703b) will possibly be degraded. When taking this point into account, an imaging point containing many patterns changed in both the x and y directions should preferably be selected as an AP. However, an AP satisfying the aforementioned condition within the area (FOV) 701b on the presupposition of the size/shape of the imaging point given by AP[p][1] (703b) does not exist (but depending on the degree of deformation possibly occurring in an actual pattern, good addressing in both the x and y directions can sometimes be assured only with the AP[p][1] (703b)).

Therefore, division of imaging point and setting of imaging sequence can be conceived, according to which two AP's such as AP[p][1] (703b) and AP[p][2] (705b) are set and for example, addressing in the y direction is once effected at AP[p][1] (703b) and subsequently addressing in the x direction is effected at AP[p][2] (705b). In the example shown in the figure, for addressing in the y direction, movement to AP[p][1] (703b) is first effected (movement 1 in the figure), followed by adjustment of both auto-focus and auto-brightness/contrast at the counterpart coordinates of AF[p][1] and ABCC[p][1] (704b) (movement 2 in the figure), movement to AP[p][2] (705b) for addressing in the x direction (movement 3 in the figure), readjustment of auto-focus at AF[p][2] (706b) (movement 4 in the figure) and final movement to EP[p] (707b) (movement 5 in the figure) for imaging. Further, in case the accuracy of stage positioning, for example, is bad or a plurality of AP's having different imaging magnifications are set, a plurality of addressing points need to be disposed. More specifically, even when a large positional shift takes place through stage shift during AP imaging, AP's are once imaged at a very low magnification so that many patterns associated with the AP's may be confined within the field of view and thereafter addressing may be effected.

With the AP's imaged at the low magnification, the accuracy of addressing is low because of the low magnification. Hence, an AP reached through beam shift is then imaged at a high magnification and detailed addressing is effected. As will be seen from the above, the present invention features that for making imaging successful, a plurality of arbitrary imaging points are disposed as necessary. In addition, the present invention also features that the disposition of plural imaging points is decided automatically as to whether to be necessary or not from CAD data or apparatus condition and if necessary, the plural imaging points are selected automatically.

Figure 7C:
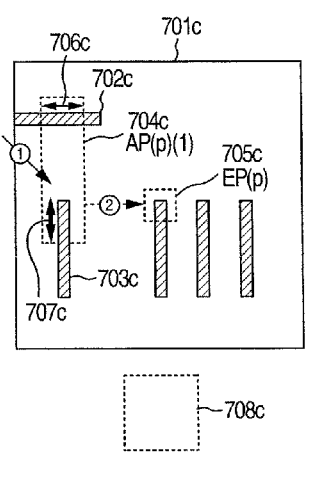
FIG. 7C is a diagram showing the imaging sequence when the shape of AP area other than square is set.

Illustrated in FIG. 7C is an example where an AP shape other than a square is set. For example, when the size/shape of an imaging range given by an imaging point 708c is presupposed, setting of an AP having high accuracies in both x and y directions is difficult to attain with a single AP. Accordingly, by enlarging the aforementioned size, an AP containing both a pattern having many edges in the x direction and a pattern having many edges in the y direction can be set. Moreover, in addition to the mere enlargement of the size of the imaging point, the shape of imaging range can be optimized such that edge lengths in x and y directions necessary for highly reliable addressing (for example, 706c, 707c) can both be included as shown at AP[p][1] (704c) (an arbitrary shape other than the rectangle is settable). The edge lengths 706c and 707c necessary for highly reliable addressing can be given by consulting a necessary condition for the selective factor index value (threshold value) which is one value of the selective processing parameter 512 the input information includes and the shape discrepancy estimative amount 513 between a design pattern and an actual pattern.

2. 3 Imaging Sequence 2 (Sharing of Imaging Point and Optimization of EP Imaging Order)

Figure 7D:
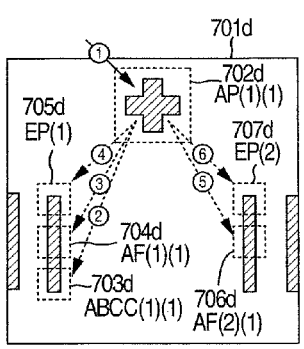
FIG. 7D is a diagram showing the imaging sequence when an imaging point is shared by a plurality of different EP's.

Illustrated in FIG. 7D is an example where imaging points are shared by a plurality of different EP's. In this example, an imaging recipe for observation of EP[1] (705d) and an imaging recipe for observation of EP[2] (707*d*) are used in common as far as possible. Firstly, addressing is effected to AP[1][1] (702*d*) (movement 1 in the figure), followed by an auto-brightness/contrast adjustment at ABCC[1][1] (703*d*) (movement 2 in the figure), an auto-focus adjustment at AF[1][1] (704*a*) (movement 3 in the figure) and then movement to EP[1] (705*d*) for imaging (movement 4 in the figure). In connection with the subsequent imaging at the EP[2] (707*d*), addressing thereto has already been finished with the AP[1][1] (702*a*) and besides the EP[2] (707*d*) is at a distance from the coordinates of the AP[1][1] through which movement based on beam shift is possible, thus omitting readdressing. In this example, the auto-brightness/contrast adjustment is also considered as not being changed largely after the execution at the ABCC[1][1] (703*d*) and is therefore omitted. The auto-focus adjustment in this example is, however, considered to be executed again before imaging at the EP[2] and so an auto-focus adjustment is made at AF[2][1] (706*d*) (movement 5 in the figure).

Finally, movement to the EP[2] (707*d*) is effected (movement 6 in the figure) and imaging is carried out. In this manner, the imaging points can be shared by the plurality of different EP's and as a result, the number of imaging operations can be reduced, thereby promoting the throughput of imaging as a whole. Therefore, the present invention features that in choosing various imaging points, the imaging point which can be shared by the plural EP's as far as possible, such as the aforementioned AP[1][1] (702*d*), is set. This can be applicable in a similar manner to the common use of an arbitrary imaging point (for an arbitrary q, common use of part or all of AP[p][q], AF[p][q], AST[p][q] and ABCC[p][q]) and the sharing by three or more EP's.

Figure 7E:
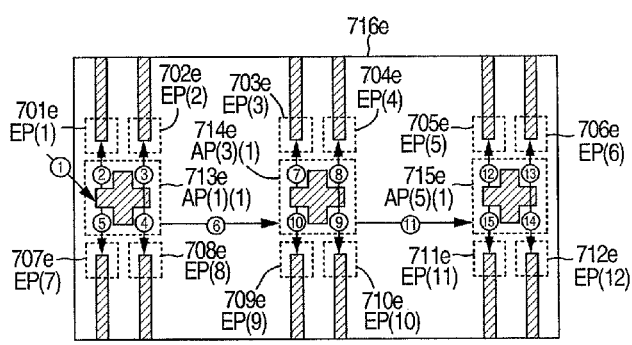
FIG. 7E is a diagram showing an example where an imaging point is shared by a plurality of EP's and correspondingly, the order of imaging the plural EP's is optimized.

Illustrated in FIG. 7E is an example where an imaging point is shared by a plurality of different EP's and correspondingly, the order of imaging the plural EP's is optimized. In this example, twelve EP[p]'s (p=1 to 12 and p being an ID allotted to each EP at will; and designated by 701*e* to 712*e* sequentially) are indicated and like the common use of imaging point explained previously with reference to FIG. 7D, AP[1][1] (713*e*) shared by the EP[1], EP[2], EP[7] and EP[8], AP[3][1] (714*e*) shared by the EP[3], EP[4], EP[9] and EP[10] and AP[5][1] (715*e*) shared by the EP[5], EP[6], EP[11] and EP[12] can be set. In this example, movement from the AP shared by the EP's to these EP's can be done through beam shift but the distance between adjacent AP's is large and movement therebetween is effected through stage movement.

In this example, when considering the order of imaging the EP[p]'s (p=1 to 12) by which high throughput can be attainable from the standpoint of the number of imaging operations, the number of processing operations and the moving distance, an order indicated at 1 to 15 in the figure (an order of EP[1], EP[2], EP[8], EP[7], EP[3], EP[4], EP[10], EP[9], EP[5], EP[6], EP[12] and EP[11]) is one of suitable imaging orders. In this imaging order, an arbitrary AP is observed and thereafter all EP's movement, to which is possible from the AP through beam shift, are all imaged sequentially, so that reiterative addressing using the same AP is unneeded and the total stage moving distance can be minimized (in this example, the stage movement is done in an order of AP[1][1] (713*a*)→AP[3][1] (714*e*)→AP[5][1] (715*e*) and is shorter than, for example, AP[1][1] (713*e*)→AP[5][1] (715*e*)→AP[3][1](714*e*)). As will be seen from above, in the present invention, the order of imaging a plurality of evaluation points can be optimized and the high throughput can be attained to advantage.

2. 4 Imaging Sequence 3 (Relief Function)

Figure 7F:
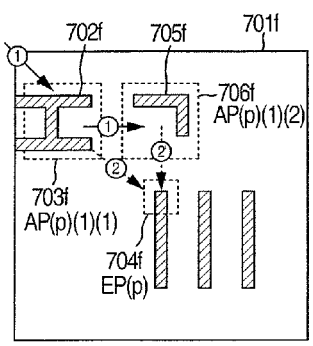
FIG. 7F is a diagram showing the relief function in the event of a failure in imaging.

Illustrated in FIG. 7F is an example of a relief function at the time of a failure in imaging. In this example, an imaging sequence is set in which addressing to AP[p][1] (703*f*) is first effected (movement 1 in the figure), followed by subsequent movement to EP[p] (704*f*) (movement 2 in the figure) for photographing. In the figure, the third arrangement number in the AP[p][1][1] indicates a number of candidate for imaging point (for AP[p][q][r] indicates an r-th candidate regarding AP[p][q]). But, when imaging the AP[p][1][1] (703*f*) actually, there is a possibility that a pattern to be as original is not formed owing to a failure as shown at, for example, an actual image template 709*f* (in the figure, for a design pattern 702*f* indicated at dotted line, a pattern 708*f* is actually formed) and because of such inconvenience, addressing fails.

Then, candidates for a plurality of different imaging points or imaging sequences are calculated in advance or at the time of occurrence of the deficiency and the processing is switched, thereby making it possible to make imaging of EP successful. Here, as an example of AP substituting for the AP[p][1][1] (703*f*), AP[p][1][2] (706*f*) is indicated. In the event that addressing to the AP[p][1][1] (703*f*) is determined to be unsuccessful through the success/failure decision, movement to the next AP[p][1][2] (706*f*) is effected (1' movement in the figure) and addressing is done. If a wiring pattern 705*f* is formed without defect and the processing succeeds, movement to the EP[p] (704*f*) is effected (movement 2' in the figure) for imaging. Further, as described previously, in order to determine how to exchange the candidates for imaging points or imaging sequences, evaluation values or preferential orders of the imaging points or imaging sequences are calculated and on the basis of the evaluation values or preferential orders, automatic changeover can be carried out.

As described above, the present embodiment features that for the sake of making imaging successful, the success/failure decision is made in processing at an arbitrary imaging point. Further, by selecting a plurality of candidates for the imaging point or reselecting them as necessary, the imaging point can advantageously be changed over in the event that the processing is determined to be unsuccessful through the success/failure decision. This can also be applied to AF, AST and ABCC in a similar way.

Figure 7G:
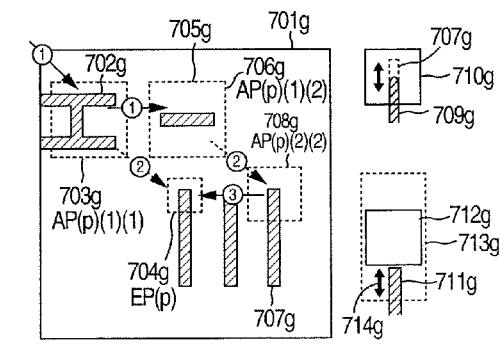
FIG. 7G is a diagram also showing the relief function in the event of a failure in imaging.

Illustrated in FIG. 7G is an example showing the relief function in the event of a failure in imaging. In the present example, the imaging sequence can be changed to a great extent by changing over the imaging point at the time of relief operation. When addressing is effected to AP[p][1][1] (703*g*) of high preferential order, for example, (movement 1 in the figure) as in the cased of FIG. 7F and the processing fails, movement to AP[p][1][2] (706*g*) of next high preferential order (1' in the figure) and addressing is effected. In the present example, however, a pattern at the AP[p][1][2] has less edge in the x direction and so AP[p][2][2] (708*g*) needs to be added (movement 2') in order to perform addressing in the y direction. In other words, it is necessary in this example that in addition to the mere change of the AP from AP]p][1][1] to AP[p][1][2], a new template be added (change from 1→2 to 1'→2'→3').

The deficiency in FIGS. 7F and 7G is a failure in addressing but in the event that deficiency takes place otherwise in imaging or processing operations, the relief can also be taken in a similar way. As described above, in the present embodiment, for the sake of making imaging successful, the success/failure decision is made in processing at an arbitrary imaging point and if the processing is determined as being unsuccessful in the success/failure decision, the imaging point or imaging sequence is switched over. This can also be applied to AF, AST and ABCC in a similar way.

Next, with reference to FIG. 7G, an example of a method of deciding which imaging point is to be switched over when imaging or processing fails will be described.

An instance will be considered in which when AP[p][2][2] (708g) is actually imaged as indicated at actual image template 710g, addressing fails because in relation to a design pattern 707g indicated at dotted line in the figure, an actually formed pattern 709g deforms to a large extent. If the actual imaging position 710 does not displaced largely from coordinates of the scheduled imaging point AP[p][2][2] (708g), it will be considered that a pattern deformation of AP[p][2][2] (708g) is problematic and as a relief function, a process for changing the AP[p][2][2] (708g) to a different imaging point (not shown) may be thought of.

On the other hand, an instance will be considered in which when imaging the AP[p][2][2] (708g) actually as shown at the actual imaging template 713a, an actually formed pattern 711g does not change largely in relation to the design pattern 707g but addressing fails on account of a large shift of the field of view. In this case, since movement to the AP[p][2][2] (708g) is based on the result of addressing to the AP[p][1][2] (706g), there is a high possibility that addressing to the AP[p][1][2] (706g) fails (or there is a possibility that an addressing before the addressing to AP[p][1][2] (706g) such as global alignment not shown fails but this is not handled by the present invention). Accordingly, in order for addressing to succeed, the AP[p][1][2] (706g) is exchanged with a different point (not shown) (in this case, the ensuing imaging sequence is also changed and the use of the AP[p][2][2] (708g) will possibly be prevented) or the size/shape of, for example, the AP[p][2][2]0 (708g) is changed so as to be exchanged with the imaging point as shown at AP (713g), thereby ensuring that even when a slight shift of imaging is generated in the y direction, addressing in the x direction based on the imaging point can be permitted because an edge length necessary for highly reliable addressing (for example 714g) cam be included in the imaging point.

As described above, the relief processing differs depending on causes of a failure. In the present invention, by adding the function to estimate causes of a failure to the success/failure decision, a more effective relief process can be selected in compliance with the failure cause. But, only the success/failure decision of imaging or processing is carried out (without estimating the cause of failure) so that in the event of a failure, a simplified relief process for mechanically switching the process to a different imaging point or imaging sequence candidate may be taken. The contents of processing in the relief process as above can be set by the operator, automatically set in the system or set by the operator on the basis of the contents processed automatically in the system.

Figure 8:
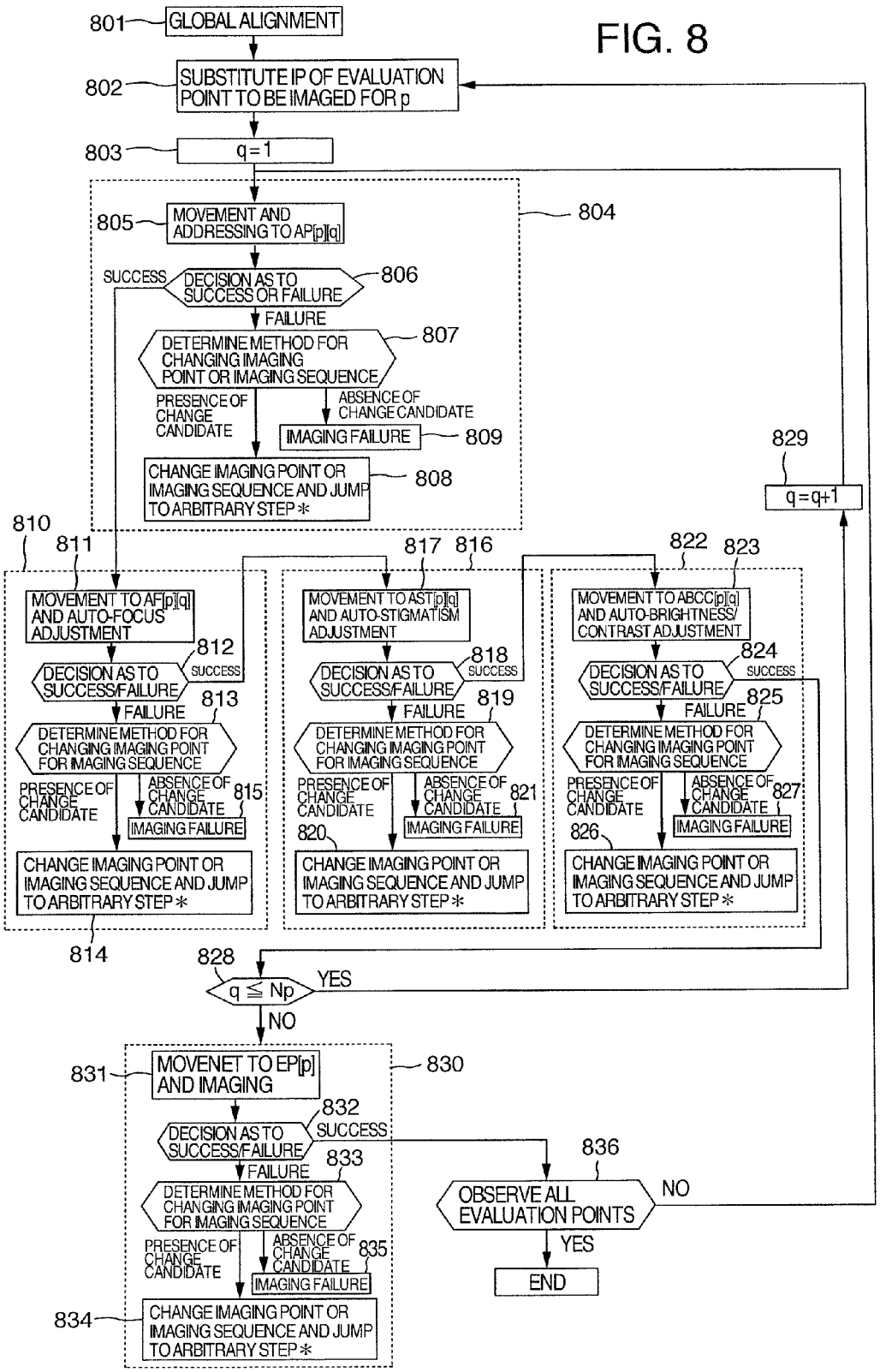
FIG. 8 is a flowchart showing the imaging sequence.

Referring now to FIG. 8, the overall imaging sequence including the relief function will be described. Firstly, in step 801, an global alignment is carried out to correct positional shift and rotation of a wafer mounted to the SEM apparatus. Thereafter, individual evaluation points EP[p] (p=1 to Np, Np≥1) are observed but the order of imaging does not always coincide with the order of ID's as shown in FIG. 7E. In step 802, p is rewritten with an ID of an evaluation point to be observed and the evaluation points are observed in accordance with the ensuing steps until observation of all evaluation points ends in step 836.

To assure good observation of the EP[p]'s, steps 803 to 829 participate in the program, whereby movement to AP, AF, AST and ABCC is effected as necessary as explained in connection with the examples of imaging sequence shown in FIGS. 7A to 7G in order that addressing (step 805), autofocus adjustment (step 811), auto-stigmatism adjustment (step 817) and auto-brightness/contrast adjustment (step 823) can be performed. After completion of the addressing, autofocus adjustment, auto-stigmatism adjustment and auto-brightness/contrast adjustment and EP imaging as well, a decision can be made as to whether the imaging or processing is successful and a relief process can be carried out in corresponding steps 806 to 809, steps 812 to 815, steps 818 to 821, steps 824 to 827 and steps 832 to 835. Here the process steps 806 to 809 following the addressing will be picked up and explained but the remaining steps may be understood similarly.

Firstly, after addressing (step 805), the addressing is decided in step 806 as to whether to be successful or not (this success/failure decision, however, includes a success/failure decision applied to a process other than the immediately preceding process. For example, in case focus adjustment in an EP image is insufficient, a focus adjustment carried out at an AF before the acquisition of the EP image is determined to be insufficient). For example, criterion for the success/failure decision is so prescribed as to determine a failure in addressing on the basis of such a phenomenon that when, in the addressing, the shift amount of maximum correlation position in the matching between an actual image template and a registry template is large, the maximum correlation value is low, the correlation distribution in the vicinity of the maximum correlation position is very gradual (there is a possibility that the maximum correlation position will be caused to change largely by a slight noise and the reliability of the estimative value of positional shift is low) or wiring pattern shapes in the two templates differ greatly from each other. Then, addressing success is determined, movement to the next imaging point is permitted (step 811 and ensuing steps) but a failure in accessing is determined, a method for changing the imaging point or imaging sequence is determined in step 807. For the purpose of determining the change method, causes of the failure can also be presumed and an efficient change method can be selected in accordance with the cause of failure.

Subsequently, when the change method is settled, the imaging point or imaging sequence is changed and p and q are changed as necessary in step 808 and thereafter, the program jumps to any one of steps 801, 805, 811, 817 and 823 to continue the imaging sequence. If no imaging point or imaging sequence change method necessary for relief is settled in the step 813, a failure in imaging results (step 815). Even in that case, the failure in imaging can be recognized and an exceptional process for exempting the failed EP image from analysis in the succeeding process can be executed. Information concerning the imaging point for which imaging or processing is successful or unsuccessful can be stored in, for example, the database 536 in FIG. 5, having linkage to the coordinate or template of the imaging point, the success/failure result or the causes of failure and can be used as history information to be consulted or utilized in the succeeding recipe creation.

In FIG. 8, the order of step blocks 810 (steps 811 to 815), 816 (steps 817 to 821) and 822 (steps 823 to 827) corresponding to the auto-focus adjustment, auto-stigmatism adjustment and auto-brightness/contrast adjustment, respectively, can be exchanged with one another arbitrarily. In respect of arbitrary p and q (p represents ID of evaluation point and q represents ID of imaging template routing in association with each evaluation point), a process of step blocks 804 (steps 805 to 809), 810 (steps 811 to 815), 816 (steps 817 to 821) and 822 (steps 823 to 827) in arbitrary combination can be omitted.

2. 5 Overall Process Flow

The overall process flow of the imaging recipe creation is summed up in FIG. 4. Firstly, in step 401, a combination of input/output information pieces is designated. Specifically, an arbitrary combination of the pieces of input/output information described in connection with FIG. 5 is possible. The input/output information combination can be set by the operator at will or a combination of defaults inside the system can be used. The default combination can be prepared in respect of a kind of wafer representing an object to be inspected or in respect of the individual steps. Next, the designated input information 402 is inputted. The input information includes at least coordinates 403 of evaluation points EP[p] (p=1 to Np, Np≥1) and CAD data 404. In addition, various other parameters 405 correspond to part of information pieces 502 to 536 designated as input information in FIG. 5. The coordinates of the evaluation point can be determined by detecting critically deficient points on a semiconductor pattern required to be inspected through, for example, pattern formation simulation in circuit design using, for example, an electronic design automation tool: ED tool) and causing the operator to conduct sampling from the detected deficient points. On the basis of the input information, the imaging point, the imaging sequence and the like are calculated (step 406. Corresponding to that in the imaging recipe automatic creation engine 501 in FIG. 5), output information 412 is outputted. In FIG. 4, three of the imaging point 413, imaging sequence 414 and evaluation value or preferential order 415 of the imaging point or imaging sequence are enumerated as the output information but through designation in the step 401, desired pieces of information among information pieces 521 to 534 in FIG. 5 can be calculated/outputted. In the step 406, on the basis of the EP[p] coordinates 403 and the movable range or forbidden range of beam shift, search ranges of various imaging points are set (step 407) and imaging points (AP/AF/AST/ABCC) are calculated (step 408).

In the step 408, the imaging point and imaging sequence are optimized (optimization of the order of EP imaging is also involved). In the step block 408, processing can be executed as necessary including the division of imaging point exemplified in FIG. 7B, the optimization of imaging sequence inclusive of common use of imaging points exemplified in FIGS. 7D and 7E (step 409 also including the optimization of EP imaging order), the optimization of the size/shape of imaging point exemplified in FIG. 7C (step 410), and the calculation of plural candidates for imaging point or imaging sequence exemplified in FIG. 7G (step 411). The output information 412, along with templates selected in the step 406 (cut out in step 417), is registered in an imaging recipe (step 418). Also, as necessary, candidates for other imaging points or imaging sequence calculated in the step 411 are registered in the imaging recipe in the step 418, registered in a different imaging recipe or managed in a database 416. In an actual imaging sequence, imaging is conducted on the basis of the aforementioned imaging recipe (step 419). If the imaging or processing of a desired imaging point in the step 419 (addressing, auto-focus adjustment, auto-stigmatism adjustment or auto-brightness/contrast adjustment) is determined to be unsuccessful in step 420, switchover to an imaging point or imaging sequence prepared in the step 418 is effected so as to make imaging or processing succeed.

3. Imaging Recipe Automatic Creation Engine

Next, an embodiment of the imaging recipe automatic creation engine 501 will be described.

3. 1 Outline of Creation Engine

Figure 9:
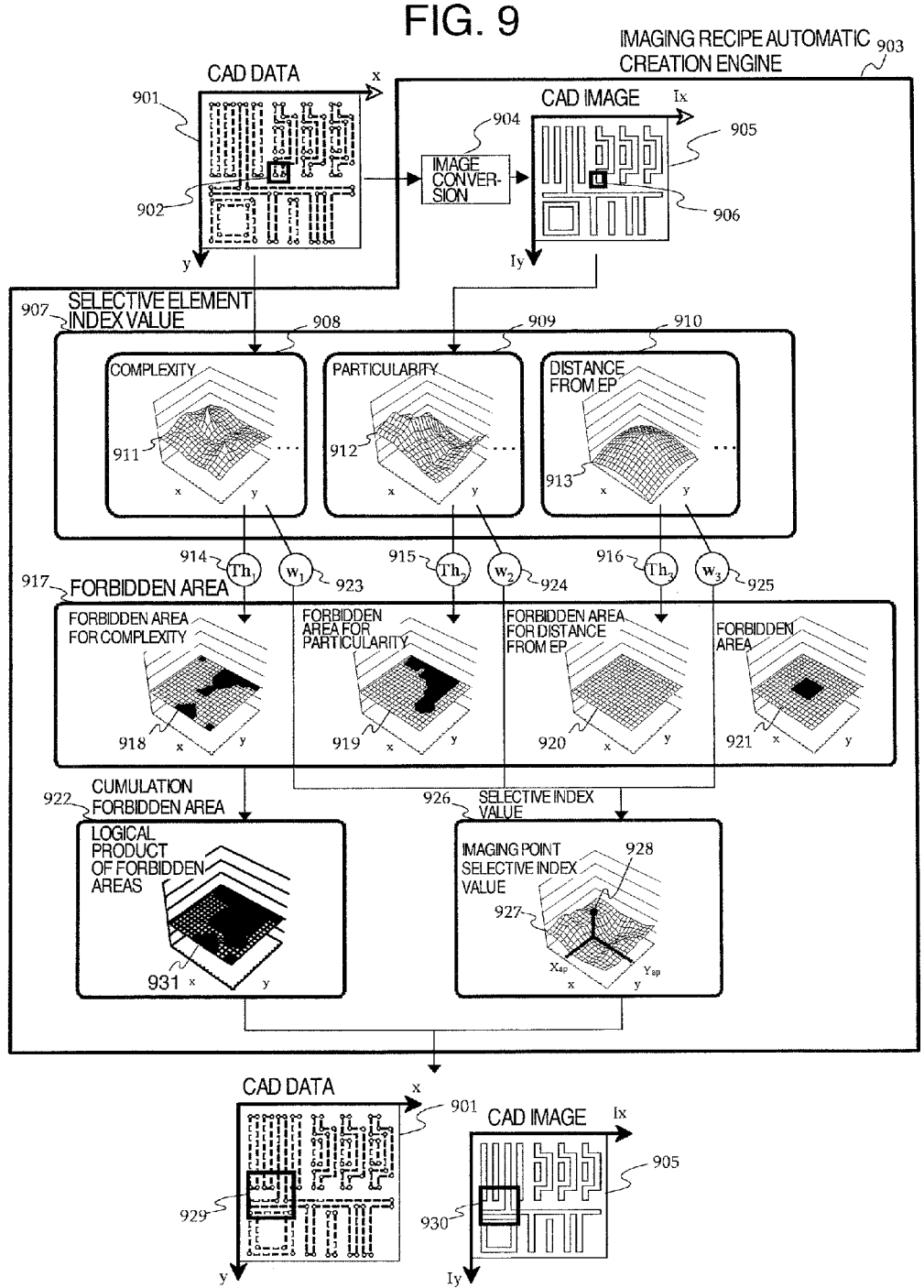
FIG. 9 is a diagram showing the contents of a process executed by an imaging recipe automatic creation engine.
Figure 10:
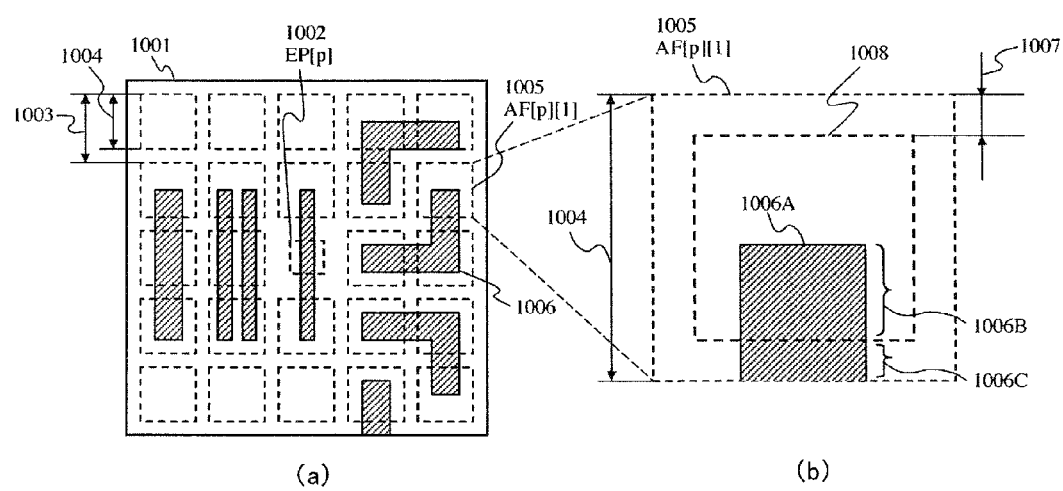
FIG. 10 is a diagram showing positions of candidates for imaging points and exaggeratedly illustrating an example of the imaging point candidate position to show a pattern range to be evaluated.

Referring now to FIG. 9, a method of evaluating/selecting a desired imaging point inside an imaging recipe creation engine 903 (501 in FIG. 5) will be described by way of example of AP selection. To sum up the process, for selection of an AP, it is necessary to evaluate if a pattern inside a desired AP is a suitable one for addressing, so that in the light of a plurality of consideration points including, for example, (1) a pattern change suitable for addressing is present in the AP (index of complexity. Distribution of the index 911), (2) because of the absence of a pattern similar to that of the AP in the vicinity of the selected AP, matching will not probably fail during addressing (index of peculiarity. Distribution of the index 912) and (3) the AP is located near an evaluation point EP (index of distance. Distribution of the distance 913), various index values at a desired imaging point candidate location are calculated (hereinafter, called selective factor index values), thus ensuring that the imaging point candidate is evaluated on the basis of the factor index values to select a proper imaging point.

3. 1. 1 Contents of Processing (Selective Factor Index Values)

The individual processing steps will be described in greater detail. Firstly, as circuit design data, CAD data 901 and EP 902 are inputted (corresponding to 404 and 403 in FIG. 4, respectively, with input information corresponding to values or range 405 of various parameters not illustrated in FIG. 9). In step 904, the CAD data 901 is converted into image data 905 (hereinafter referred to as CAD image. Details of this step will be described later with reference to FIGS. 12A and 12B).

Next, in step 907 in FIG. 9, a selective factor index value at each imaging point candidate is calculated. In FIG. 9, distributions 911 to 913 of three selective factor index values are illustrated as an example but an arbitrary number of selective factor index values designed pursuant to various evaluation criteria can be calculated. In each of the selective factor index value distributions 911 to 913, the value of each selective factor index value when the center of an AP exists at arbitrary x and y coordinates (x, y) in the CAD data coordinates is expressed in terms of wire frame (a coordinate system indicating evaluation positions can also be expressed by x and y coordinates (Ix, Iy) in the CAD image as a result of conversion of the CAD data into an image which substitutes for arbitrary x and y coordinates in the CAD data coordinates). As will be described later, from the standpoint of required calculation accuracy and calculation time, the selective factor index value can be calculated by using CAD data 901 as input information or by using CAD image 905 as input information.

In step 908, the selective factor index value is calculated using the CAD data 901 as input information and in step 909, it is calculated using the CAD image 905 as input information. In step 910, however, the selective factor index value is calculated using neither the CAD data 901 nor CAD image 905 as input information. Although, in the steps 908 to 910, only respective ones of selective factor index values 911 to 913 are illustrated, a plurality of arbitrary selective factor index values can be calculated in an arbitrary one or ones of the steps 908 to 910 and, like the illustrated selective factor index values, can be used as materials for decision of imaging point selection. In each of the selective factor index value distributions 911 to 913, the larger the value (the value in z direction orthogonal to the x and y axes being larger), the better the obtained evaluation can be but the relation between the magnitude of index value and the quality (better/worse) of evaluation can be changed in respect of individual selective factor index values.

For example, in a conceivable method of collectively deciding the plurality of selective factor index values to select a selecting (imaging) point, an overall selective index value is calculated (distribution of the index values is designated at 927) from the linear sum, designated at 926, of the selective factor index values (a value obtained by multiplying the individual factor index values 911 to 913 by weights w1 to w3 (923 to 925 and adding the products) and an imaging point is determined on the basis of the overall selective index value (for example, an imaging point centered on coordinate values (Xap, Yap) 928 at which the overall selective index value is maximal is determined as an AP).

An example of the AP selected through the above process is illustrated at lower part of FIG. 9. The AP can be delivered as either a range or FOV 929 on the CAD data 901 or a range 930 on the CAD image 905. The weights w1 to w3 are of one type of selective process parameter 512 in FIG. 5 and advantageously, by changing the weight, the selection criterion of various imaging points can be customized. The AP selection process shown in FIG. 9 can be applied in a similar way to selection of the imaging points AF, AST and ABCC other than the AP by making an exchange with selective factor index values for evaluating a criterion to be satisfied by each imaging point.

From values of the selective index value 927 or selective factor index values 911 to 913, propriety of an arbitrary imaging point can be evaluated quantitatively and so evaluation values or preferential order at the plural candidates for imaging point or imaging sequence can be calculated. Further, through the decomposition into indexes and the evaluation in consideration of plural points of view as in the case of the selective factor index values, an arbitrary imaging point can be decided as to mere its propriety/impropriety and besides causes of the propriety/impropriety can be analyzed and therefore the arrangement of imaging points and the determination of imaging sequence can be settled.

3. 1. 2 Contents of Process (Forbidden Area)

By using setting of a forbidden area for objects excluded from the imaging point selection in combination with the above-described selection process, high accuracy of selection can be attained. A description will be given of the forbidden area hereunder.

Firstly, by setting a forbidden area in consideration of the beam shift moving range and a forbidden area in consideration of the influence of contamination at the EP, candidates for an imaging point to be selected can be restricted (step 921). In an example of the forbidden area in consideration of the beam shift movable range, when movement is required from an arbitrary selected imaging point, for example, AP[1][1] (1302) to EP[1] (1303) through beam shift as shown in FIG. 13A, the range of searching the AP is set to the interior of a beam shift movable range 1304 centered on the EP[1] (1303). In this case, a forbidden area is given as hatched area 1305 to keep an imaging point such as AP from being selected from the interior of area 1305. Thus, an AP selected from the interior of area 1304 satisfies a condition for movability to the EP through beam shift.

In another example of the forbidden area, when especially selecting an imaging point to be picked up at a high magnification with the aim of restraining deposition of contamination on, for example, EP[1] (1303) (with the electron beam irradiated on the specimen for a long period of time, a contaminative substance is deposited on the specimen), an imaging area for the EP[1] (1303) and its neighboring area 1306 can be set as a forbidden area (the imaging range of the EP is prohibited from overlapping an imaging range of a different imaging point. Setting of the neighboring area is effected in order that even if a slight positional shift occurs at the different imaging point, overlapping on the EP can be avoided). The search range and the forbidden area can be designated by the user at will or by a rule of default in the system (one of values of selective process parameter 512 in FIG. 5).

Further, the aforementioned forbidden area for restraining the contamination deposition can be set in consideration of a plurality of EP's. As an example to this effect, an instance will be considered in which as shown in FIG. 13B, imaging is first effected at EP[1] (1303) and thereafter, EP[2] (1307) representing the next evaluation point is imaged. If, in the course of selection of an AP for the EP[1] (1303), the AP is searched on the condition that only the forbidden area 1306 provided nearby the EP[1] (1303) is avoided as has been explained in connection with FIG. 13A, there is a danger that an AP[1][1] (1309), for example, is selected as the AP. Through imaging of the AP[1][1] (1309), contamination will be deposited within an imaging range of the EP[2] (1307) to be imaged subsequently and therefore selection of the AP[1][1] (1309) is not reasonable for imaging of the EP[2] (1307). Accordingly, in selecting an AP for the EP[1] (1303), the AP[1][1] must be selected on the condition that both a set of imaging area EP[1] (1303) and its neighboring forbidden area 1306 and a set of imaging area EP[2] (1307) and its neighboring forbidden area 1308 are avoided. The above forbidden area setting method can be applicable similarly to the case where three or more EP's are considered or selection of AF, AST and ABCC is effected.

The present embodiment features setting of a forbidden area in consideration of plural EP's. Distribution of forbidden areas set according to the teachings of FIGS. 13A and 13B is indicated at forbidden area 921 in FIG. 9. In the forbidden area 921, (x, y) coordinates of imaging points prohibited for selection are indicated in black. This type of indication method is also applicable to forbidden areas 918 to 920 to be described later.

Next, a forbidden area to be set by using the selective factor index value will be described. For example, in respect of individual selective factor index values 911 to 913, evaluation values to be satisfied at the least for an imaging point (here AP) are set as threshold values Th1 to Th3 (914 to 916), respectively, imaging points having selective factor index values not satisfying the above threshold values are set as forbidden areas so as to be excluded from candidates and an imaging point can be determined from the residual candidates on the basis of the selective factor index value 927. The threshold values Th1 to Th3 are one of values of selective process parameter 512 in FIG. 5 and by changing the threshold values, the selection criteria for various imaging points can be customized to advantage. Candidates below the threshold values Th1 to Th3 (914 to 916) set for the selective factor index values 911 to 913 are set as forbidden areas, as exemplified at 918 to 920 in FIG. 9. In the figure, areas in which the selective factor index values do not satisfy the criteria are forbidden areas as indicated in black. In this example, the area of less than the threshold value is set as the forbidden area but, in some case, depending on designed selective factor index value, the smaller the value, the better the evaluation can be and in this case, an area of larger than the threshold value is set as a forbidden area. Further, as typified by the forbidden area 920 corresponding to the selective factor index value 913, setting may also be made such that no forbidden area is set depending on the threshold value. A forbidden area 931 is the logical sum of the forbidden area 921 and the forbidden areas 918 to 920 corresponding to the individual selective factor index values and an AP is selected from an area exclusive of the forbidden area 931.

3. 2 Selective Factor Index Value

There are plural selective factor index values (three are exemplified in FIG. 9) as described previously and the present invention features that for calculation of the selective factor index values, the CAD data or CAD image is selectively used as input information in respect of the individual selective factor index values. Namely, the CAD data is the coordinate data that has highly accurate coordinates but has only contour information as data, being unsuitable for evaluation of a two-dimensional pattern. On the other hand, the CAD image is of a quantized image that has lower shape accuracy than the CAD data but is effective to evaluate the matching characteristic of two-dimensional templates. Further, depending on the contents of processing, the processing speed sometimes differs for the CAD data and CAD image. As will be seen from the above, the data format (coordinate data or image data) for expressing design data is advantageous or disadvantageous from the viewpoint of the processing accuracy or processing speed for an arbitrary processing and hence in the calculation of the selective factor index value, information of different data format such as CAD data or CAD image is utilized selectively in accordance with the selective factor index value to calculating the selective factor index value, thereby assuring compatibility between a proper index value calculation accuracy and a proper calculation speed.

Enumerated in FIG. 9 are an example where the index value is calculated by using the CAD data as input information in the selective factor index value 911 blocked at 908, an example where the index value is calculated by using the CAD image as input information in the selective factor index value 912 blocked at 909 and an example where the index value without resort to input information in the form of the CAD image and CAD data for calculation is indicated in the elective element index value 913 blocked at 910.

These combinations are a mere example and as the case may be, the selective factor index value 912 can be so set as to be calculated by using the CAD data as input information. Although not illustrated, there can possibly be a selective factor index value using both the CAD data and CAD image. Furthermore, in FIG. 9, only one kind of selective factor index value is calculated in each of the blocks 908 to 910 but there can possibly be a case where a plurality of kinds of selective factor index values are calculated or a case where no index value is calculated.

Turning to FIG. 10(a), there are illustrated CAD data 1001 in which areas possible movement thereto from EP 1002 are cut out, and positions of candidates for imaging points to be evaluated (represented by 5×5=25 template areas typified by a dotted block at 1005). The number, size (1004)/shape (square area in the figure) of the imaging point candidates to be evaluated and the distance (1003) of an imaging point to be evaluated to an adjacent one can be set at will. Depending on the size or distance of the imaging point, areas of the imaging point candidates will sometimes overlap on one another. The imaging point candidate 1005 in FIG. 10(a) is illustrated exaggeratedly in FIG. 10B. For example, in selecting an AP, it is decided whether an addressable pattern is sufficiently included in an area of the imaging point candidate. At that time, in consideration of a view-field shift for an imaging point due to the positioning accuracy of the imaging position change method (stage shift or beam shift), an estimative amount of view-field shift 1007 (part of the apparatus conditions 514 in FIG. 5) is given so that the imaging point size 1004 may partly be cut by the view-field shift estimative amount 1007 and a selective factor index value may be calculated from only a pattern included in an inner area 1008, thereby ensuring that an imaging point free of imaging failure and processing failure can be selected to advantage even if the view-field shift occurs. In FIG. 10(b), a pattern 1006A is contained in the imaging point candidate area 1005 but only a partial pattern 1006B of pattern 1006A, which can be included in the field of view without fail even in the presence of the view-field shift estimative amount 1007, is evaluated as to whether to be a pattern suitable for addressing.

Next, a variation of the CAD data or CAD image serving as an input when the selective factor index value is calculated will be described. As an example, CAD data 1201 of a ring-form pattern is illustrated in FIG. 12A (indicated by apexes of pattern contour and dotted line connecting adjacent apexes). In an actual pattern, there is a possibility that the pattern is so deformed as to have its corners rounded as compared to the CAD data because of variations in manufacture parameters. If the pattern shape is evaluated from only the CAD data without taking such a discrepancy in shape between the CAD data and the actual pattern, there is a danger that the accuracy of calculation of the selective factor index value is degraded. Accordingly, for approximation to the actual pattern shape, modified CAD data 1202, for example, is created by obliquely cutting corners of the CAD data 1201 and by using the modified CAD data 1202, a selective factor index value can be calculated. Otherwise, a location where there is a high possibility that the discrepancy between the CAD data and the actual pattern becomes large can be excluded from evaluation at the time of calculation of the selective factor index value.

Modifying methods other than the aforementioned oblique cutting of corners may be enumerated including rounding corners or thinning the overall pattern and the kind of method and the degree of modification can be set arbitrarily (the modifying method and degree can be designated according to the shape discrepancy estimative amount 513 between the design pattern and the actual pattern in FIG. 5). A CAD image 1203 can be created from either the CAD data 1201 or the modified CAD data 1202. Further, from the created CAD image 1203, for example, a CAD image 1204 can be created having its pattern zone painted on the basis of mask extraction residue information (508 in FIG. 5) or a modified CAD image 1205 applied with image processing such as a smoothing process can be created. In FIG. 12A, the images 1202, 1204 and 1205 can be omitted in arbitrary combination. For calculation of the selective factor index value, the data 1201 to 1205 can be taken in arbitrary combination so as to be used as input information in respect of each selective factor index value.

Turning now to FIG. 12B, a method of creating a CAD image from CAD data will be described by way of example of creation of a CAD image 1203 from the CAD data 1202. In making an image, the screen is divided by an image quantization width 1206 into a pixel lattice and a pixel, over which a line segment of the pattern 1202 exists, is changed in its brightness to make an image (as exemplified by hatched pixel 1207). The image quantization width (pixel/nm) 1206 (one of processing parameters 512 in FIG. 5) is geometrically dimensioned so as to keep an arbitrary analytical process (imaging process to be executed after image conversion) from being put to inconvenience.

Figure 14A:
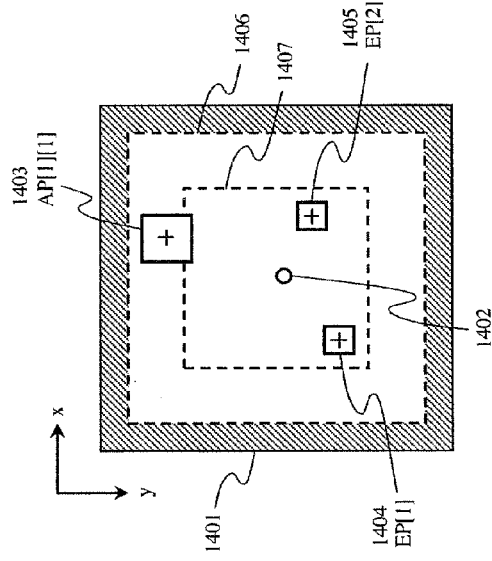
FIG. 14A is a diagram showing an AP shared by a plurality of different EP's.
Figure 14B:
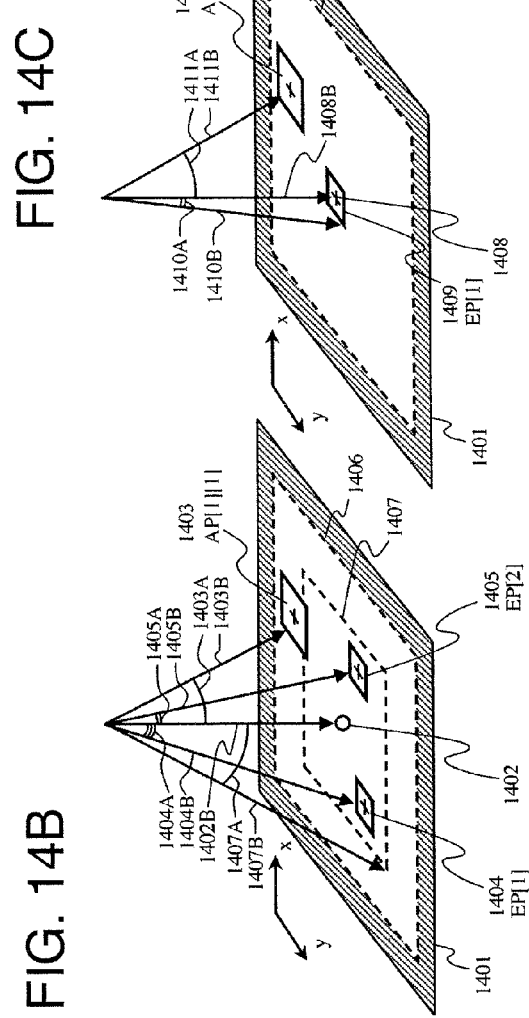
FIG. 14B is a diagram showing incident angles of an electron beam when plural EP's and an AP which are at coordinates different from electron beam vertically incident coordinates are imaged.

By making reference to FIGS. 14A to 14C, an example of selection of a shared AP will be described by way of an instance where an imaging point is shared by a plurality of different EP's as exemplified in FIGS. 7D and 7E. In the case of evaluation of an AP candidate sharable by the plural EP's, too, various selective factor index values are calculated in essentiality for individual AP candidates as in the case of selection of AP for a single EP described previously and the AP selection is conducted on the basis of the index value. In FIG. 14A, a common AP 1403 is selected for sharing by two EP's 1404 and 1405, whereby addressing to the common AP 1403 is carried out by movement thereto through stage shift and thereafter sequential movement to the EP's 1404 and 1405 is conducted through beam shift, followed by imaging thereat.

Figure 14C:
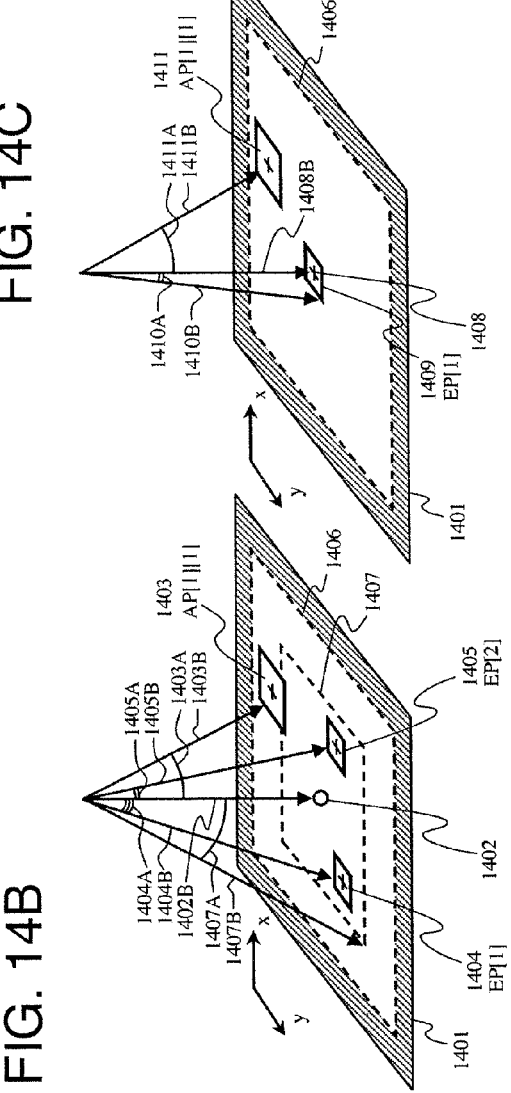
FIG. 14C is a diagram showing electron beam vertical incident coordinates and incident angles of an electron beam when imaging EP, AP.

In typical observation of EP, to assure that the electron beam can be irradiated on the overall EOV plane of EP 1409 as from vertically above the wafer surface as possible as shown in FIG. 14C, it is frequent that the irradiation position on the wafer surface of an electron beam 1408B landing in an incident direction vertical to the wafer surface (called electron beam vertical incident coordinates) is so set as to be substantially brought to an FOV center 1408 of the EP. In other words, an electron beam 1410B landing on the edge of FOV of the EP under a tilt angle 1410A making to the vertically incident electron beam 1408B is deemed as being at the most tilted position among the electron beam irradiation positions inside the EP but this tilt angle can be minimized.

But when the plural EP's are imaged sequentially by merely effecting the sequential movement through beam shift as described previously, it is difficult to cause the electron beam to be vertically incident on all centers of FOV of the plural EP's. Therefore, when a common AP shared by a plurality of EP's is set, electron beam vertically incident coordinates 1402 must be determined pursuant to some method as shown in FIG. 14B (FIG. 14B is a diagram when FIG. 14A is viewed sideways thereof). The present invention features that on conditions that for example, movement of the EP's to be imaged and the imaging point as well from the electron beam vertically incident coordinates 1402 is possible through beam shift, the incident angle of the electron beam when imaging the EP's and imaging point is smaller than a permissible electron beam incident angle to be described later and the imaging point can be shared as many EP's as possible, not only the electron beam vertically incident coordinates 1402 but also imaging points such as the EP's by which the AP is shared and the AP are determined. Illustrated in FIG. 14B is an example where two EP's 1404 and 1405 are imaged by using a common AP 1403 and incident angles of the electron beam when imaging centers of the individual templates are designated by 1403A, 1404A and 1405A, respectively.

The present invention also features that the permissible electron beam incident angle can be set in respect of the kind of each template and EP (one of values of requested picture quality 517 in FIG. 5). Under the limit condition at the least, imaging can be permitted within a range 1406 of movement from the electron beam vertically incident coordinates through beam shift but with the picture quality and the accuracy of various processes using picked-up images as well in mind, the beam incident angle preferably approximates verticality and so the search range of each template can be narrower than the range 1406. Especially at the EP, measurement of a highly accurate pattern shape is conducted and therefore, in comparison with the AP, for example, requirements for the permissible electron beam incident angle are sometimes stringent. In FIG. 14B, inputting of the AP is exemplified so that the AP may be selected from the moving range 1406 based on beams shift and the EP's may be selected from a separately designated range 1407. The input designation can be fulfilled in the form of either permissible electron beam incident angle 1407A or the range 1407 spreading from the electron beam vertically incident coordinates 1402.

3.3 Registry Template

Figure 15A:
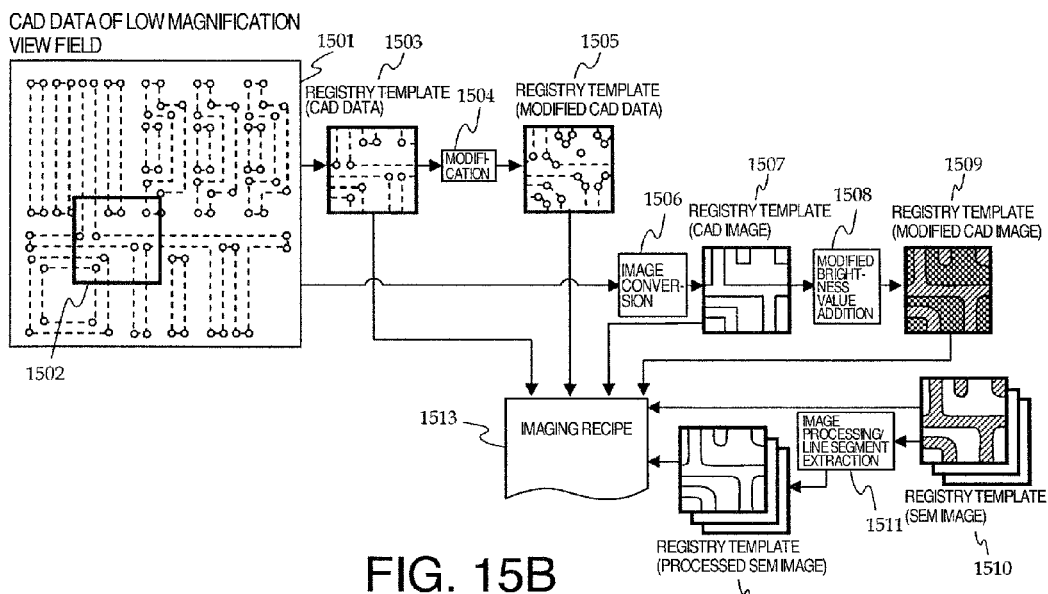
FIG. 15A is a diagram for explaining a method of registering templates of a selected imaging point in the imaging recipe.
Figure 15B:
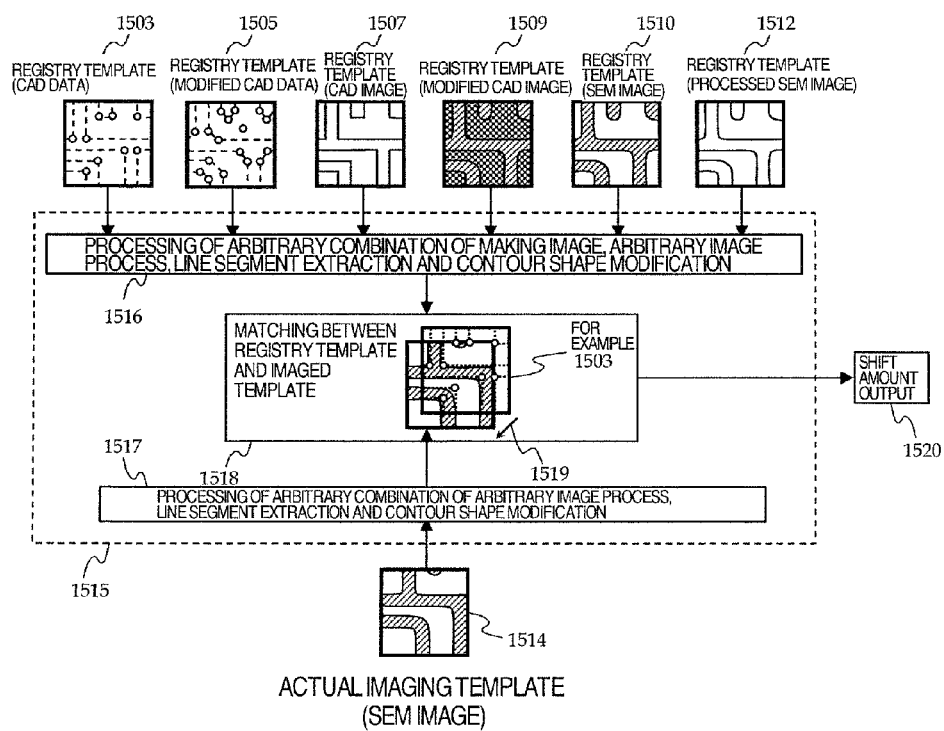
FIG. 15B is a diagram showing a variation of a process for matching between a registry template and an actual image template.

A description will be given of a method for registering a template of an evaluation point or a selected imaging point in the imaging recipe by making reference to FIG. 15A.

An instance will be considered in which an arbitrary imaging point 1502 is selected in CAD data 1501. As an example for explanation, the imaging point 1502 is assumed to be an AP. For registration of the AP 1502 in an imaging recipe 1513, the following six methods can be listed up.

(1) CAD data (coordinate data) corresponding to the imaging point 1502 cut out of the CAD data 1501 is registered as a registry template in the imaging recipe 1513.

(2) Modified CAD data 1505 obtained by adding an arbitrary modification 1504 (for example, the previously described modification shown at 1202 in FIG. 12A) to the CAD data (coordinate data) corresponding to the imaging point 1502 cut out of the CAD data 1501 is registered as a registry template in the imaging recipe 1513.

(3) A CAD image 1507 obtained by applying image conversion 1506 (for example, the previously-described making image indicated in FIG. 12B) to the CAD data corresponding to the imaging point 1502 cut out of the CAD data 1501 is registered as a registry template in the imaging recipe 1513.

(4) A modified CAD image 1509 obtained by applying arbitrary modification/brightness addition 1508 (for example, the previously-described modification/brightness addition indicated at 1204 and 1205 in FIG. 12A) to the CAD image 1507 as a result of the image conversion 1506 (for example, the previously-described image making in FIG. 12B) applied to the CAD data corresponding to the imaging point 1502 cut out of the CAD data 1501 is registered as a registry template in the imaging recipe 1513.

(5) An SEM image 1510 at the above imaging point acquired by actually imaging an arbitrary imaging point is registered as a registry template in the imaging recipe 1513.

(6) An SEM image 1512 obtained by applying an arbitrary imaging process to the SEM image 1510 at the aforementioned imaging point as a result of actual imaging of an arbitrary imaging point is registered as a registry template in the imaging recipe 1513. Exemplified as the imaging process is a smoothing process of image, a noise elimination process or a line segment extraction process. When the line segment extraction process is executed, the SEM image 1512 is processed to line segment information.

The present invention features that any one of templates of the above (1) to (6) formats is selectively registered in the imaging recipe or arbitrary ones of these templates are registered in combination in the imaging recipe. The presence of a plurality of variations in the format of a template, for example, an AP template to be registered in the imaging recipe has an advantage that speedup of a matching process between a registry template used for addressing an imaging position in the actual imaging sequence and an actually imaged template can be assured and highly accurate matching can be attained.

In a method of processing matching (1515) between the registry template and the actually imaged template, various variations can be thought of. In a method, for example, image matching (1518) between image information of a registry template (for example, template 1507, 1509, 1510 or 1512, an image as a result of application of an arbitrary process 1516 to the template 1507, 1509, 1510 or 1512 or template 1503, 1505 or 1512 subjected to making image through the process 1516) and image information of an actually imaged template (template 1514 or template as a result of application of an arbitrary image process 1517 to the template 1514) is executed, whereby a positional shift amount 1519 can be calculated and the shift amount can be delivered (1520). In another method, line segment matching (1518) between line segment information of a registry template (for example, line segment information extracted from a template 1503, 1505 or 1512, a template as a result of application of the arbitrary process 1516 to the template 1503, 1505 or 1512 or a temple 1507, 1509, 1510 or 1512 subjected to line segment extraction through the process 1516) and line segment information of an actually imaged template (line segment information extracted from the template 1514 through the process 1517) is executed, whereby a positional shift amount 1519 can be calculated and the shift amount can be delivered (1520).

As described above, the template subject to the arbitrary process 1516 (arbitrary imaging process or shape modification, or conversion to an arbitrary data format) is sometimes used in matching and so by saving, in the imaging recipe, a template undergone the arbitrary process 1516 in accordance with the matching method, the arbitrary process 1516 need not be carried out each time the matching process is conducted to thereby speedup the processing. Further, arbitrary ones of the registry templates 1503, 1505, 1507, 1509, 1510 and 1512 can be saved in combination in the imaging recipe.

4. System Constitution (Database Management, Sharing)

An embodiment of apparatus constitution in the present invention will be described with reference to FIGS. 16A and 16B.

Figure 16A:
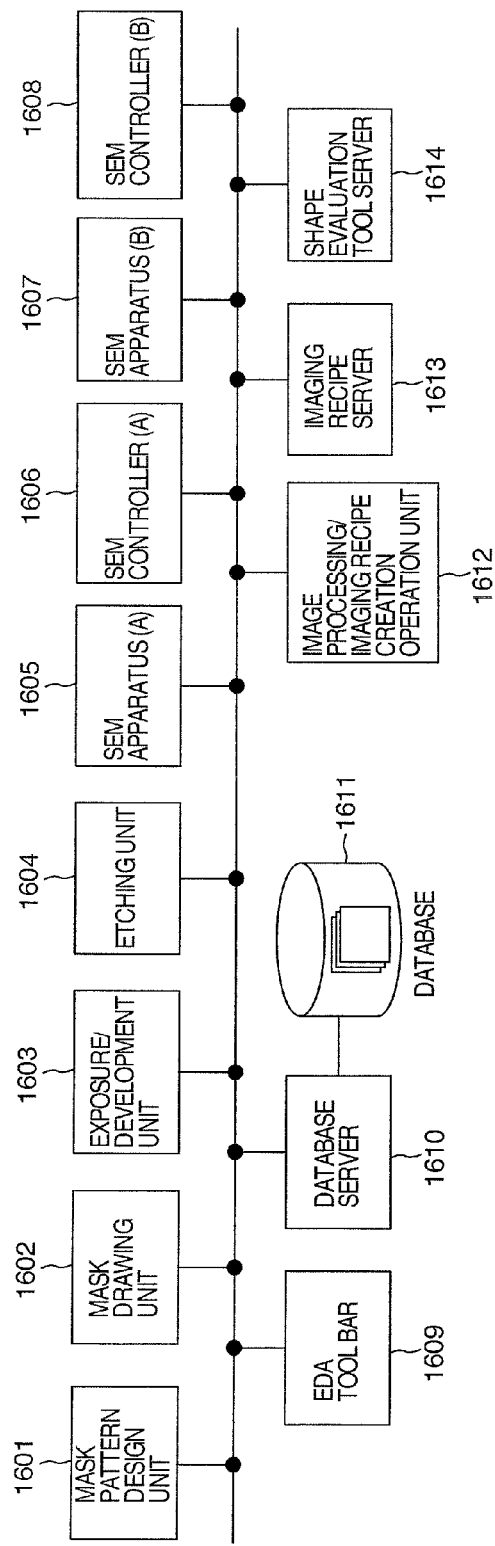
FIG. 16A is a diagram showing an example of construction of an apparatus system.

The apparatus shown in FIG. 16A comprises a mask pattern design unit 1601, a mask drawing unit 1602, a mask pattern exposure/developing unit 1603, an etching unit 1604, SEM apparatus 1605 and 1607, SEM control units 1606 and 1608 for controlling the SEM apparatus 1605 and 1607, respectively, an EDA (electronic design automation) tool bar 1609, a database server 1610, a storage 1611 for saving the database, an image process/imaging recipe creation operation unit 1612, an imaging recipe server 1613 and an evaluation tool server 1614 for evaluating a created pattern shape (for making a comparison between shapes of, for example, SEM image data and design data of the evaluation pattern). The components as above can transmit/receive information through a network.

The storage 1611 attached to the database server 1610 can save default value, setting value and calculation value of arbitrary input/output information shown in FIG. 5 by linking them to the product kind, manufacture date and time and success/failure results of imaging or processing and also can consult the saved data. In the figure, as an example, the two SEM apparatus 1605 and 1607 are connected to the network but in the present invention, the imaging recipe can be shared by a plurality of arbitrary SEM apparatus by way of the data server 1611 or imaging recipe server 1613 and with an imaging recipe once created, the plural SEM apparatus can be operated. When the database is shared by the plurality of SEM apparatus, the success/failure results of old imaging or processing can be stored speedily and the stored data can be consulted to assist in excellent imaging recipe creation.

Figure 16B:
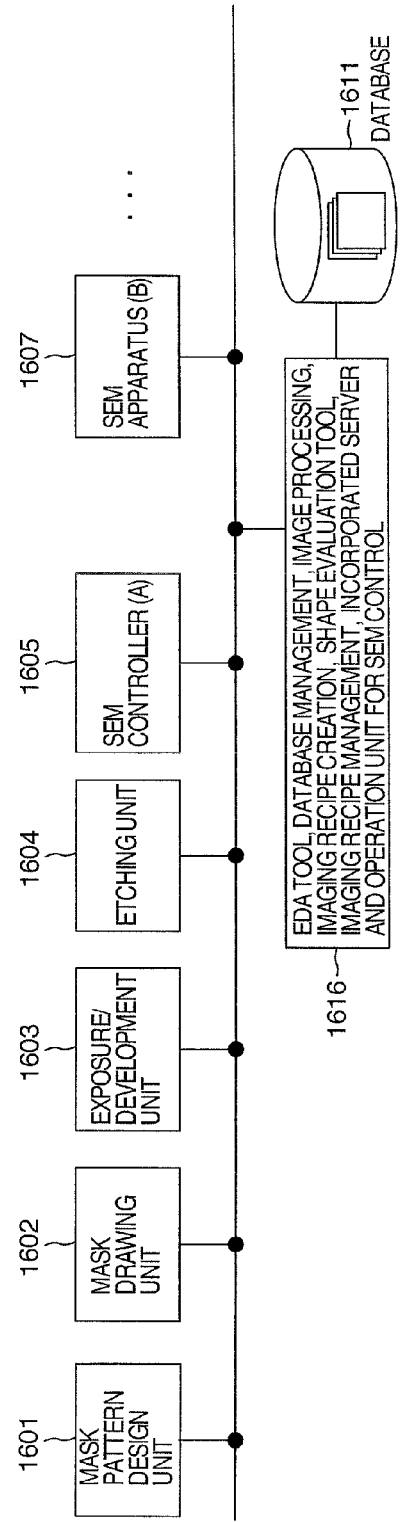
FIG. 16B is a diagram showing another example of construction of the apparatus system.

The embodiment shown in FIG. 16A can be modified as shown in FIG. 16B in which the components 1606, 1608, 1609, 1610 and 1612 to 1614 are incorporated in a single unit 1616. As in this modification, it is possible to process arbitrary functions by distributing them to arbitrary plural units or incorporating them in a single unit.

5. GUI

Figure 11:
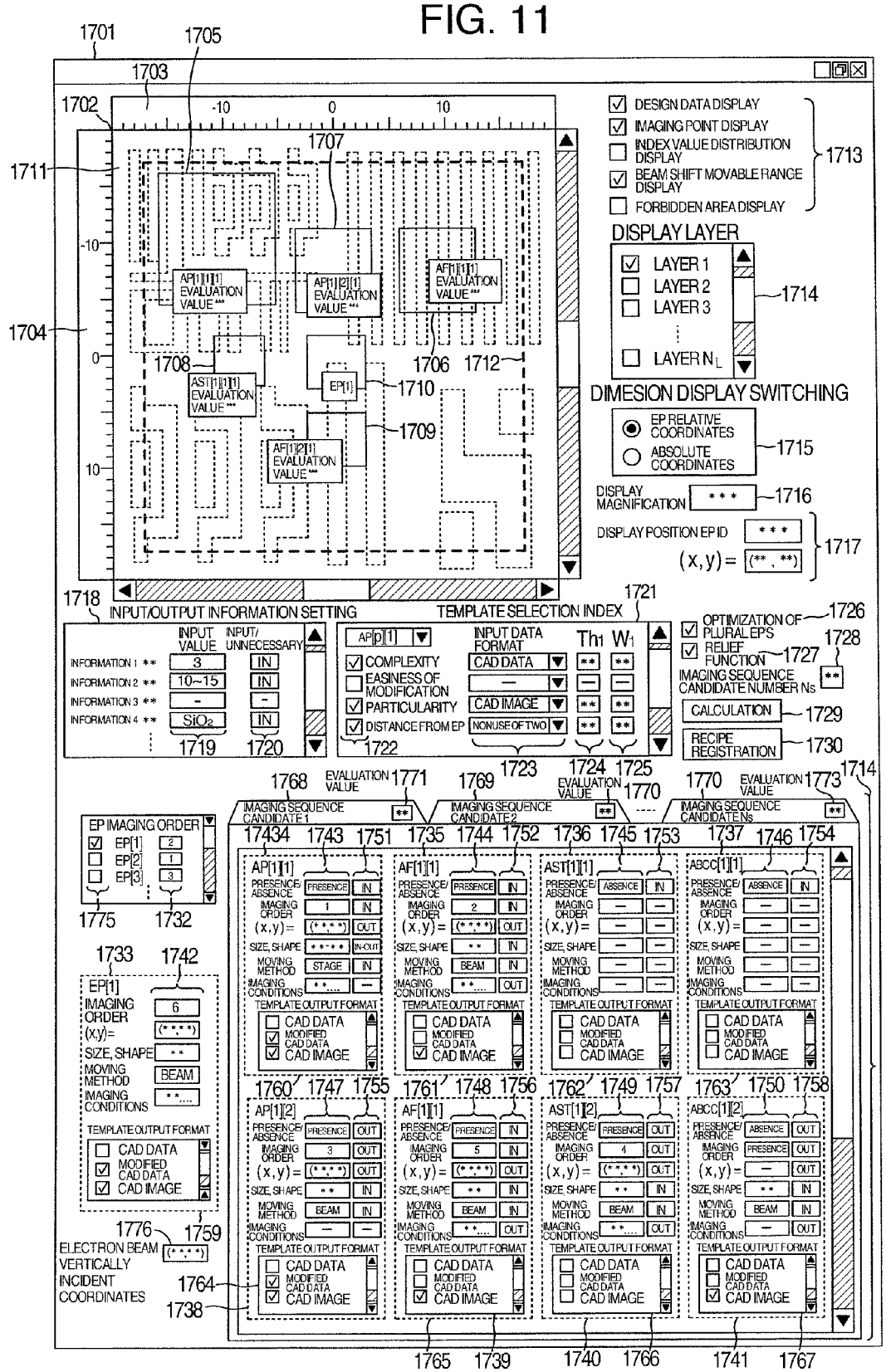
FIG. 11 is a diagram showing a GUI screen.

Reverting to FIG. 11, an embodiment of the GUI for setting input/output information or displaying the results in the present invention will be described. As shown at a window 1701 in FIG. 11, various kinds of information to be described below can be displayed allover the screen or divisionally by means of a monitor, for example. In FIG. 11, mark * indicates an arbitrary numerical value (or letter string) or a range of numerical value, or arrangement of numerical value or numerical value range inputted or outputted to or from the system. Setting of input information will be described.

In a window 1718, the information pieces 506 to 519 shown in FIG. 5 are enumerated (indicated as information 1, 2, ... in the figure) and the enumerated individual information pieces 506 to 519 are designated in box 1720 as to whether to be used as input information to the imaging recipe automatic creation engine or not. In the box 1720, information entered as "IN" indicates input information and information entered as "-" is not handled as input information. To the information designated as input information, its numerical value or numerical value range or name (for example, kind, process, material) can be designated in box 1719.

In a window 1721, the selective factor index values such as complexity and easiness of deformation (for example, 911 to 913 in FIG. 9. In addition, a selective factor index value based on other evaluation criterion may be included) are enumerated and arbitrary selective factor index values to be evaluated in respect of individual imaging point kinds (q-th AP, AF, AST and ABCC) designated by a box 1775 can be selected in combination by using a check box 1722 (as an example, three selective factor index values of "complexity", "peculiarity" and "distance from EP" are selected in FIG. 11). Further, on the basis of the chosen selective factor index values, threshold values Thi (i=1 to Nt, Nt≥1. For example, 914 to 916 in FIG. 9) for setting a forbidden area and weights Wi (i=1 to Nw, Nw≥1) for calculation of selective index value (for example, 923 to 925 in FIG. 9) can be designated by means of boxes 1724 and 1725, respectively. Besides, an input data format used for calculation of the respective selective factor index values can be chosen from, for example, a pull-down menu 1723. Specifically, it can be designated that as the input information for calculation of the selective factor index values, the CAD data is used, the CAD image is used, both the CAD data and the CAD image data are used or none of the CAD data and CAD image is used.

Further, an instance will be possible in which as represented by the division of addressing point previously shown in FIG. 7B, a proper imaging point cannot be selected with selective process parameters such as threshold value Thi and weight Wi initially designated in the window 1721 (for example, with the parameters supposing addressing by a single addressing point) and the selective process parameters are required to be changed (for example, to parameters supposing addressing by two addressing points). Accordingly, depending on conditions, the user can designate a plurality of selective process parameters or such an instance as above can be determined automatically inside the system and the selective process parameters can be changed automatically.

By ON/OFF checking a check box 1726, a choice can be made as to whether an imaging point is shared by a plurality of EP's as explained in connection with FIG. 7D or as to whether the optimization process of imaging template selection is executed by taking the positional relation among plural different EP's into account as typified by setting of a forbidden area in consideration of plural EP's explained in connection with FIG. 13B can be selected.

By ON/OFF checking a check box 1727, a choice can be made as to whether the process of switching the imaging point or imaging sequence is executed by considering the relief function explained in connection with FIGS. 7F and 7G. Namely, with the check box 1727 checked ON, the success/failure of the process at each imaging point is decided and in the case of a failure of the process, causes of the failure are presumed so that a candidate for the imaging point or imaging sequence necessary for switching the imaging point or imaging sequence may be determined in accordance with the failure causes.

A box 1728 can designates the number of candidates when determining the plural imaging sequence candidates in advance for the sake of relief function. In a window 1733, items 1742 concerning the individual evaluation points EP[p] (p=1 to Np, Np≥1) are designated (in the figure, EP[1] is indicated but the items can be settable for EP[p] corresponding to an arbitrary arrangement number p). Designated as the items are coordinates (x, y) of each evaluation point EP[p] (p=1 to Np, Np≥1), the size/shape of imaging point, the moving method (beam shift or stage shift) and the imaging condition. These items may be designated in arbitrary combination. Then, in a window 1759, the data format of a registry template for EP[p] to be registered in the imaging recipe can be designated.

The data format is represented by the CAD data, modified CAD data, CAD image, modified CAD image, SEM image and modified SEM image and arbitrary ones may selectively be combined so as to be registered as a template or conversely, no template can be registered (outputted). Electron beam vertically incident coordinates can be inputted to or outputted from a box 1776. For example, in case the imaging sequence is optimized with a single EP, the electron beam vertically incident coordinates can be so designated as to be identical to the center coordinate of the EP or in case the imaging sequence inclusive of an imaging point shared by plural EP's is optimized, the electron beam vertically incident coordinates can be optimized inside the imaging recipe automatic creation engine and then outputted to the box 1776.

Next, in an area 1774, information designative as input information is set in respect of an arbitrary imaging point (imaging points AP[p][q], AF[p][q], AST[p][q] and ABCC[p][q] subject to a q-th processing in observation of a p-th evaluation point). In the figure, as an example of imaging points, AP[1][1], AF[1][1], AST[1][1], ABCC[1][1], AP[1][2], AF[1][2], AST[1][2] and ABCC[1][2] are displayed in order of 1734 to 1741 but the method for designation of the input information is the same for these imaging points and so the AP[1][1] 1734 will particularly be taken and described hereunder.

As illustrated, in the items 1734, the presence or absence of imaging point setting (in the case of absence, AP[1][1] is not set), imaging order of imaging point, coordinates (x, y) of imaging point, size/shape of imaging point (area), moving method (beam shift or stage shift) and imaging condition are included and arbitrary ones can be designated in combination. For information whose value is designated, the value (inclusive of a letter string) is entered in a corresponding item 1743 on the right and "IN (ID of input information)" is entered in a box 1751. Here, a range of values can be entered in item 1743 and a proper value within the range can be outputted by means of the imaging recipe automatic creation engine. For example, a process can be conceivable in which the size of AP[1][1] is so designated as to be set within a range of 3 to 10 μm and the engine outputs a size of 5 μm as a proper value. In this case, the value range is entered in the item 1743 and "IN-OUT (ID of input and output information) is entered in the box 1751. Further, like the aforementioned window 1759 of EP[p], the data format of a registry template for AP[1][1] to be registered in the imaging recipe can be designated in a window 1760.

Next, a description will be given of setting of output information. For the output information, "OUT (ID of output information)" is entered in corresponding one of the boxes 1751 to 1758. Information used as neither input information nor output information is designated by entering "- (ID of unused information)" in corresponding one of the boxes 1751 to 1758.

When a button 1729 is depressed, the imaging recipe automatic creation engine calculates output information on the basis of a combination of input/output information pieces designated in the manner described previously to indicate the output information to the items 1743 to 1750 in association with the respective boxes 1751 to 1758 on which "OUT" or "IN-OUT" is entered.

In the FIG. 11 example, in accordance with the user command or the default value, necessity is set for AP[1][1], AF[1][1] and AF[1][2] and needlessness is set for AST[1][1] and ABCC[1][1] whereas the imaging recipe automatic creation engine is so designated as to be caused to output the presence/absence of setting for AP[1][2], AST[1][2] and ABCC[1][2] so that the results of output of the imaging recipe automatic engine may indicate that necessity is set for the AP[1][2] and AST[1][2] and needlessness is set for the ABCC[1][2]. Further, the output stipulates the imaging sequence (order of imaging the imaging points) such that AP[1][1]→AF[1][1]→AP[1][2]→AST[1][2]→AF[1][2]→AP[1][2]→EP[1] stands. Further, the evaluation value or preferential order of the imaging sequence can be indicated in a box 1771. The evaluation value quantitatively determines the degree of success of imaging the EP[1] pursuant to the imaging sequence and can be calculated on the basis of, for example, a selective index value (929 in FIG. 9) at the imaging point involved in the imaging sequence.

A plurality of candidates for imaging sequence can be calculated and in the figure, Ns imaging sequence candidates 1768 to 1770 are delivered (no results are shown after 1769 but for example, by clicking a corresponding tag, an indication can be obtained like 1768). An imaging point at an r-th imaging sequence can be indicated by, for example, AP[p][q][r] (in the figure, $3^{rd}$ parameter inscription is omitted). The above description is given particularly by way of the EP[1] but a similar process can be applied to each evaluation point EP[p] (p=1 to Np).

By turning ON the box 1726, the order of imaging the EP[p] (p=1 to Np) can be optimized and delivered to a box 1732 in a window 1731. In the example shown in the figure, the output is so stipulated as to perform imaging in an order of EP[2]→EP[1]→EP[3]. In this manner, as typified by sharing of an imaging point by plural EP's explained using FIG. 7D, the reduction of the number of imaging operations (the number of imaging points) and the shortening of the view field moving distance can be assured through the sharing and optimization of imaging order of EP[p], thus realizing high throughput throughout the observation of all of the plural EP[p]'s.

A designated or outputted imaging point can be confirmed in a window 1702. By setting ON/OFF of check box group 1713 in the window 1702, design data, various imaging points, selective factor index values or distribution thereof, beam shift movable range and forbidden area can be indicated in arbitrary combination. In the figure, coordinates and size/shape of respective imaging points are indicated at 1705 to 1710. In connection with the respective imaging points, the selective factor index value or selective index value or preferential order value can be indicated together with the indications 1705 to 1710.

In a display 1711 of CAD data, through layer selection in a window 1714, an arbitrary combination of layers can be displayed in a overlapping fashion. Gauges 1703 and 1704 describing dimensions around the display 1711 of CAD data can be displayed. By designation through a radio button 1715, relative coordinates from the EP or absolute coordinates on the chip can be indicated at the gauges 1703 and 1704. Also, the display magnification and the display position center in 1702 can be designated in boxes 1716 and 1717, respectively. The center of display position can be designated by p representing ID of EP[p] (so that the designated EP[p] may be brought to the center of the screen and displayed thereat) or by coordinate value (x, y). Further, in place of the display 1711 of CAD data, an actually imaged SEM image can otherwise be displayed.

With a button 1730 depressed, information of inputted or outputted imaging point or imaging sequence and a registry template can be delivered to the imaging recipe. In this case, plural imaging point candidates or plural imaging sequence candidates can be delivered to a single imaging recipe or can be divided so as to be delivered to a plurality of imaging recipes.

The imaging recipe automatic creation method, the imaging point evaluation method or display method (GUI) or the file management method and system constitution according to the present invention set forth so far can be utilized in not only the SEM but also the optical microscope or scanning probe microscope (SPM). In other words, even in the optical microscope or SPM, AP, AF and EP are sometimes required to be set and this requirement can be dealt with by changing the evaluation criterion of selective factor index value described in the present invention. The optical microscope can also be utilized for automatic search of global alignment mark from CAD data in the step 302 in FIG. 3. In the SPM, the SEM image described so far corresponds to depth information acquired with the SPM or conversion of the depth information into an image (the value of depth is converted into a brightness value of the image).

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

The invention claimed is:

1. A method for imaging by a scanning electron microscope system, the method comprising the steps of:
    inputting, into the system, coordinates of a plurality of evaluation points of a specimen to be inspected;
    setting a plurality of addressing points, wherein an addressing direction of an element in a first addressing point differs from an addressing direction of an element in a second addressing point;
    determining an imaging sequence that includes the plurality of evaluation points and the plurality of addressing points; and
    imaging the specimen to be inspected, according to the imaging sequence.

2. A method of imaging according to claim 1, wherein the plurality of addressing points include: a first addressing point with an element disposed in an x-axis addressing direction, and a second addressing point with an element disposed in a y-axis addressing direction, or vice versa.

3. A method of imaging according to claim 1, wherein a design layout of the specimen is rendered as an input, and the respective positions of the plurality of addressing points, are determined in accordance with the design layout.

4. A method of imaging according to claim 3, wherein a determination of whether or not there an addressing point exists is set as each evaluation point is inspected.

5. A scanning electron microscope system, comprising:
    an inputting means for inputting, into the system, coordinates of a plurality of evaluation points of a specimen to be inspected;
    a setting means for setting a plurality of addressing points, wherein an addressing direction of an element in a first addressing point differs from an addressing direction of an element in a second addressing point;
    a determining means for determining an imaging sequence that includes the plurality of evaluation points and the plurality of addressing points; and
    an imaging means for imaging the specimen to be inspected, according to the imaging sequence.

6. A scanning electron microscope system according to claim 5, wherein the plurality of addressing points include: a first addressing point with an element disposed in an x-axis addressing direction, and a second addressing point with an element disposed in a y-axis addressing direction, or vice versa.

7. A scanning electron microscope system according to claim 5, wherein a design layout of the specimen is rendered as an input, and the respective positions of the plurality of addressing points, are determined in accordance with the design layout.

8. A scanning electron microscope system according to claim 7, wherein a determination of whether or not an addressing point exists is set as each evaluation point is inspected.

9. A method of imaging according to claim 2, wherein the plurality of addressing points include an addressing point with both an element disposed in an x-axis addressing direction and an element disposed in a y-axis addressing direction.

10. A scanning electron microscope system according to claim 6, wherein the plurality of addressing points include an addressing point with both an element disposed in an x-axis addressing direction and an element disposed in a y-axis addressing direction.

* * * * *